US005553609A

United States Patent [19]
Chen et al.

[11] Patent Number: 5,553,609
[45] Date of Patent: Sep. 10, 1996

[54] INTELLIGENT REMOTE VISUAL MONITORING SYSTEM FOR HOME HEALTH CARE SERVICE

[75] Inventors: Yaobin Chen; Thomas G. Mintun, both of Indianapolis, Ind.

[73] Assignees: Visiting Nurse Service, Inc., Indianapolis; Indiana University Foundation, Bloomington, both of Ind.

[21] Appl. No.: 386,015

[22] Filed: Feb. 9, 1995

[51] Int. Cl.$^6$ ........................................................ A61B 5/02
[52] U.S. Cl. ............................ 128/630; 128/670; 128/904
[58] Field of Search ..................................... 128/630, 670, 128/904, 633, 677, 683; 348/6, 13, 14, 16, 148

[56]  References Cited

U.S. PATENT DOCUMENTS

| | | | |
|---|---|---|---|
| 4,831,438 | 5/1989 | Bellman, Jr. et al. | 358/108 |
| 4,838,275 | 6/1989 | Lee | 128/670 |
| 4,843,377 | 6/1989 | Fuller et al. | |
| 4,962,473 | 10/1990 | Crain | |
| 4,965,819 | 10/1990 | Kannes | |
| 5,036,852 | 8/1991 | Leishmann | 128/630 |
| 5,086,385 | 2/1992 | Launey et al. | |
| 5,144,661 | 9/1992 | Shamosh et al. | |
| 5,192,999 | 3/1993 | Craczyk et al. | |
| 5,202,759 | 4/1993 | Laycock | |
| 5,291,399 | 3/1994 | Chaco | |
| 5,301,105 | 4/1994 | Cummings, Jr. | |
| 5,319,363 | 6/1994 | Welch et al. | 340/825.36 |
| 5,412,708 | 5/1995 | Katz | 348/14 |
| 5,416,695 | 5/1995 | Stutman et al. | 364/413.02 |

Primary Examiner—Angela D. Sykes
Assistant Examiner—Stephen Huang
Attorney, Agent, or Firm—Woodard, Emhardt, Naughton, Moriarty & McNett

[57]  ABSTRACT

A computer-based remote visual monitoring system is provided for in-home patient health care from a remote location via ordinary telephone lines. The system includes a supervisory control center having access to patient and health care professional databases for assigning patients to appropriate health care professionals and for performing task planning. A number of master monitoring computers are linked to the control center and are accessible by a corresponding number of health care professionals. A slave monitoring computer is located within the homes of a plurality of patients and may be linked via telephone modems to any of the master monitoring computers. Audio/visual equipment at both locations permits real-time two-way communications during an "in-home" visit to a patient by a health care professional from a remote location. The health care professional has control over the audio/visual equipment in the patient's home as well as the communication of multimedia data via the master monitoring computer, and may automatically generate and maintain the patient's multimedia medical records.

51 Claims, 20 Drawing Sheets

351 —

VISITING NURSE SERVICE CHHA CHARTING
P-ID: 2    Date Reviewed: 10/14/94    Date Notified: 10/14/94

Date Visited: 10/14/94        Time Visited: 9:00 A.M.

Document Actual Findings — 350
- [X] Temperature: 115.00     [X] Pulse: 67
- [X] Respirations: y         [ ] B/P: b

Bathing/Dressing — 352
- [ ] Frequency (Per Week): 0
- Partial or Complete: [ ]    Type:(Bed/Tub/Sink/Shower): [ ]

354 —
- [ ] Shave: [ ]              [X] Mouthcare: tre — 356

Haircare — 358
- [X] Shampoo: g              [X] Comb Brush: g

Nailcare (Not for Diabetics) — 360
- Fingernails(Clean, Trim): [ ]   [X] Toenails(Clean, Trim): [ ]

362 — [ ] Footcare(TH=Ted Hose; s=Soak): [ ]

Range of Motion — 364
- Extremity/IES Involved: [X]  Active: [ ]   [X] Passive: [ ]

366 — [ ] Medication Assistance: [ ]    [ ] Toileting: [ ] — 368

370 — [ ] Ambulation/Transfer Assistance: [ ]

[ ] Skin Care (Lotion/Massage): [ ] — 371

372 — [ ] Linen Change: [ ]    [ ] Make Bed: vcdvcbc — 374

[ ] Light Housekeeping (Immed. Area): [ ]
— 376

380 — [X] Meal Preparation: [ ]

Diet Instructions: bcvb — 382
Activity: bcvbcvbcvb — 384
Special Procedure Instructions: [ ] — 386

388 — Call RN for Changes in Condition or Problems, such as: [ ]    Initials: [ ]

392 — RN Assigning Care: [ ]    Voice Mail #: 0 — 390

394 — Narrative Notes and/or Change in Condition: [ ]

Signature: *Nurse*

P-ID: [1]   215   416   418   [Close]
IV Date Visited: [6/22/94]   Time Visited: [10:40:00 A.M.]

Visit Type: — 420
- Initial: ☐   Resume/Readmit: ☐
- Eval Only: ☐   CHHA Supervision: ☐   Subsequent: ☐

Vital Signs: — 422
- T: [0]   P(r): [0]
- P(a): [0]   R: [0]   B/P: [0]   WT: [0]

Other Significant Data/Problems: [ ] — 426

Medicine Teaching: — 424
- Taught to: [ ]
- List MED Name [ ] [ ]
- with Codes 1: [ ] [ ]
- Takes Meds as Ordered: ☐
- Reason (for no): [ ]
- Verbalizes Understanding: ☐ [ ]
- Needs Review: ☐ [ ]

CHHA Supervision: — 428
- No CHHA: ☐   POC Appropriate: ☐
- POC Not Appropriate, Assignment Changed: ☐
- POC Followed AEB: ☐ [ ]
- POC Not Followed AEB: ☐ [ ]
- CHAA MGR Contacted: ☐
- Rapport: [ ]

Functional Limits: [ ]   — 430
Last/Next MD Visit: [ ]
Others Present: [ ]
Discharge planning: [ ]
Plan for next visit: [ ]

1): — 432
- Priority Goals: [ ]
- Target Date: [ ]
- Assessments: [ ]
- Teaching/Interventions: [ ]
- Response/Progress: [ ]

2): — 434
- Priority Goals: [ ]
- Target Date: [ ]
- Assessments: [ ]
- Teaching/Interventions: [ ]
- Response/Progress: [ ]

IV Date Visited: 6/22/94   Time Visited: 10:40:00 A.M.

Skill:

Close

Return Demonstration    Comments

- ☐ Basic principles of sterile technique:
- ☐ Proper handwashing:
- ☐ Proper storage of solution or supplies:
- ☐ Preparing clean work area:
- ☐ Adding medications to the solution:
- ☐ Filling tubing with fluid or medication:
- ☐ Connecting tubing to medication container:
- ☐ Principles of fluid flow and adjustment of rate pump setting:

- ☐ Using SASH technique to flush catheter:
- ☐ dressing changes and site care:
- ☐ Medication dosage and possible side effects:
- ☐ Troubleshooting and problem solving:
- ☐ Disposal of used sharps and other supplies:

- ☐ Basic principles of sterile technique:
- ☐ Proper handwashing:
- ☐ Proper storage of solution or supplies:
- ☐ Preparing clean work area:
- ☐ Adding medications to the solution:
- ☐ Filling tubing with fluid or medication:
- ☐ Connecting tubing to medication container:
- ☐ Principles of fluid flow and adjustment of rate pump setting:

- ☐ Using SASH technique to flush catheter:
- ☐ dressing changes and site care:
- ☐ Medication dosage and possible side effects:
- ☐ Troubleshooting and problem solving:
- ☐ Disposal of used sharps and other supplies:

- ☐ Basic principles of sterile technique:
- ☐ Proper handwashing:

INTELLIGENT REMOTE VISUAL MONITORING SYSTEM FOR HOME HEALTH CARE SERVICE

FIELD OF THE INVENTION

This invention relates generally to a system and method for providing home health care services, and more particularly to such a system for permitting health care professionals to provide "in-home visits" with patients using a communications system transmitting multimedia data via ordinary telephone lines.

BACKGROUND OF THE INVENTION

The concept of home health care began in the 1850's when traveling health care professionals provided in-home visits to patients in need of health care and unable to seek such care on their own. From the outset, however, the home health care system suffered from the problem of "downtime" in traveling to a patient's home to deliver the service needed. In modern times, this problem has been compounded by the shortage of health care professionals providing home health care and by rising medical costs. In fact, nowadays it is often impossible for a home health care professional to justify the costs of performing supervisory or teaching visits, and home health care visits are, too often, limited to basic needs or medical emergencies.

Health care costs in the United States, which now consume 15% of GDP, have been increasing at a rate significantly higher than inflation. In many other industries, new technology has been developed to increase productivity and reduce costs. In health care, however, technology has been used primarily to advance scientific knowledge and improve the quality of care.

According to a recent report from the Hudson Institute, it is estimated that, due to increased health care costs, work force shortages and increased longevity, the United States has a time span of approximately ten years to develop a coordinated national health care plan to be able to care for the dependent population. If a workable health care service delivery system is not in place by then, the population demographics may make it nearly impossible to expect a marked decrease of persons in the labor pool to generate the means to provide health/home care. This crisis will be heightened as the baby boomers become older and the manpower in every discipline continues to dwindle. A critical need therefore exists for new technology to be developed which will have the effect of reducing the cost of health care while improving the quality of the health care system.

SUMMARY OF THE INVENTION

One solution to the foregoing health care problems is to develop cost-effective home care technologies that enable the delivery of health care outside the hospital environment and nursing home. The remote visual monitoring system of the present invention is one such technology that solves at least some of the problems facing the home health care industry by greatly reducing costs while enabling home health care professionals to provide quality home health care.

In accordance with one aspect of the present invention, a remote monitoring system for permitting a health care professional to provide health care to a patient in the patient's home from a remote location comprises a main database system including a first database having patient data stored therein and a second database having health care professional data stored therein; a supervisory control computer in communication with the main database system, wherein the supervisory control computer has means for assigning at least one patient in the first database to a health care professional in the second database for providing health care thereto; a master monitoring computer located remote from the patient's home and in communication with the supervisory control computer, wherein the master monitoring computer has a first telephone modem associated therewith for transmitting and receiving data and the master monitoring computer is operable to provide a plurality of operator command signals at the first modem in response to a corresponding plurality of operator commands provided by the health care professional; and a slave monitoring computer located in the patient's home, wherein the slave monitoring computer has a second telephone modem associated therewith for transmitting and receiving data, and the slave monitoring system is in communication with the master monitoring computer via a telephone link established between the first and second modems, and wherein the slave monitoring computer is responsive to the plurality of operator command signals to transmit real-time multimedia data relating to the patient to the master monitoring computer; wherein the health care professional may provide real-time health care to the patient in the patient's home from a remote location.

In accordance with another aspect of the present invention, a remote monitoring system for permitting a health care professional to provide health care to a patient in the patient's home from a remote location comprises a video camera located in the patient's home, wherein the video camera provides video signals in accordance with video images captured thereby and is responsive to a plurality of control signals to perform a corresponding plurality video camera functions; a master monitoring computer located remote from the patient's home, wherein the master monitoring computer has a first telephone modem associated therewith and a monitor, and the master monitoring computer receives the video signals from the video camera and displays the corresponding video images on the monitor, and further provides the plurality of control signals to the video camera in response to corresponding operator commands provided by the health care professional; and a slave monitoring computer located in the patient's home, wherein the slave monitoring computer has a second telephone modem associated therewith and is in communication with the master monitoring computer via a telephone link established between the first and second modems, and the slave monitoring computer receives the video signals from the video camera and provides the video signals to the master monitoring computer via the telephone link, and further receives the plurality of control signals from the master monitoring computer and provides the control signals to the video camera; wherein the health care professional may control the video camera functions in real time from a remote location to thereby provide an aspect of home health care by viewing the patient at various locations within the patient's home.

In accordance with yet another aspect of the present invention, a remote monitoring system for permitting a health care professional to provide health care to a patient in the patient's home from a remote location comprises means located within the patient's home for generating multimedia data relating to the patient; a slave monitoring computer located in the patient's home, wherein the slave monitoring computer has a first telephone modem associated therewith for transmitting and receiving data, and the slave monitoring computer receives the multimedia data and transmits the multimedia data at the first modem; a first database having multimedia patient data stored therein; and a master monitoring computer located remote from the patient's home, wherein the master monitoring computer has a monitor and a second telephone modem associated therewith for transmitting and receiving data, and the master monitoring computer is in communication with the slave monitoring computer via a telephone link established between the first and second modems, and wherein the master monitoring computer receives the multimedia data at the second modem and displays the multimedia data on the monitor, the master monitoring computer further being responsive to an operator command signal corresponding to an operator command provided by the health care professional to automatically store the multimedia data within the first database to thereby maintain a multimedia medical log of the patient's medical treatment; wherein multimedia medical data relating to the patient and generated within the patient's home may be received and maintained by a health care professional from a remote location.

In accordance with a further aspect of the present invention, a method of providing health care to a patient in the patient's home from a remote location comprises the steps of: (1) providing a first computer at the remote location; (2) providing a second computer in the patient's home; (3) linking the first and second computers to each other for communication therebetween; (4) providing means for generating real-time multimedia data relating to the patient within the patient's home; (5) transmitting the real-time multimedia data relating to the patient to the first computer; (6) observing the patient in real-time from the remote location via the multimedia data relating to the patient; and (7) communicating with the patient in real-time via the communications link to thereby provide the patient with health care from the remote location.

In accordance with yet a further aspect of the present invention, a remote monitoring system for permitting a health care professional to provide health care to a patient in the patient's home from a remote location comprises a robot located in the patient's home, wherein the robot is responsive to a plurality of control signals to perform a corresponding plurality of health care related functions; a master monitoring computer located remote from the patient's home, wherein the master monitoring computer has a first telephone modem associated therewith and provides the plurality of control signals to the robot in response to corresponding operator commands provided by the health care professional; and a slave monitoring computer located in the patient's home, wherein the slave monitoring computer has a second telephone modem associated therewith and is in communication with the master monitoring computer via a telephone link established between the first and second modems, wherein the slave monitoring computer receives the plurality of control signals from the master monitoring computer and provides the control signals to the robot; wherein the health care professional may control the robot functions in real time from a remote location to thereby provide an aspect of home health care by performing any of the plurality of health care related functions via the robot.

In accordance with still another aspect of the present invention, a remote monitoring system for permitting a health care professional to provide health care to a patient in the patient's home from a remote location comprises a sensor located in the patient's home, wherein the sensor is responsive to a control signal to sense a bodily condition of the patient and to provide a sensor signal corresponding to the sensed condition, a master monitoring computer located remote from the patient's home, wherein the master monitoring computer has a first telephone modem associated therewith for providing the control signal to the sensor in response to a corresponding operator command provided by the health care professional and the master monitoring computer receives the sensor signal via the first modem and has means associated therewith for determining the bodily condition from the sensor signal, and a slave monitoring computer located in the patient's home, wherein the slave monitoring computer has a second telephone modem associated therewith and is in communication with the master monitoring computer via a telephone link established between the first and second modems. The slave monitoring computer receives the control signal from the master monitoring computer and provides the control signal to the sensor so that the health care professional may control said sensor in real time from a remote location to thereby provide an aspect of home health care by determining the bodily condition.

In accordance with yet another aspect of the present invention, a remote monitoring system for permitting a health care professional to provide health care to a patient in the patient's home from a remote location comprises an actuator located in the patient's home, wherein the actuator is responsive to a control signal to actuate and deactuate a home feature, a sensor associated with the actuator, wherein the sensor senses the operating status of the home feature and provides a sensor signal corresponding thereto, a master monitoring computer located remote from the patient's home, wherein the master monitoring computer has a first telephone modem associated therewith for providing a control signal to the actuator in response to a corresponding operator command provided by the health care professional and the master monitoring computer receives the sensor signal via the first modem and has means associated therewith for determining the operating status of the home feature from the sensor signal; and a slave monitoring computer located in the patient's home, wherein the slave monitoring computer has a second telephone modem associated therewith and is in communication with the master monitoring computer via a telephone link established between the first and second modems. The slave monitoring computer receives the control signal from the master monitoring computer and provides the control signal to the actuator so that the health care professional may control the home feature in real time from a remote location to thereby provide an aspect of home health care.

One object of the present invention is to provide an audio/visual communication system whereby a health care professional may conduct an "in-home" visit with a patient from a location remote from the patient's home.

Another object of the present invention is to permit the health care professional to control various audio/visual equipment located within a patient's home during an "in-home" visit, and in real-time, so that the health care professional may see and hear various locations and events within the patient's home.

Yet another object of the present invention is to provide a health care professional with the ability to generate and maintain a multimedia medical chart relating to various patients.

Still another object of the present invention is to provide a health care professional with the ability to control a robot located within a patient's home, in real-time, to permit the health care professional to perform a variety of medical and home-care related functions.

A further object of the present invention is to provide a health care professional with the ability to control bodily condition sensors located within a patient's home, in real-time, to permit the health care professional to detect a variety of bodily conditions.

Still a further object of the present invention is to provide a health care professional with the ability to control home features located within a patient's home, in real-time, to permit the health care professional to assist a patient in controlling home appliances, home environmental features and the like.

These and other objects of the present invention will become more apparent from the following description of the preferred embodiment.

BRIEF DESCRIPTION OF THE DRAWINGS

FIG. 14 is an expanded graphical representation of the Charting Review option of FIG. 13.

FIG. 16 is a graphical representation of a Clinical Notes option within the user interface program.

FIG. 17 is an expanded graphical representation of the Clinical Notes option of FIG. 16.

FIG. 20 is a graphical representation of an instructional care form option within the user interface program for providing instructions on intravenous care.

FIG. 21 is an expanded graphical representation of the Intravenous care form of FIG. 20.

FIG. 22 is a graphical representation of a Visit Log form option within the user interface program.

DESCRIPTION OF THE PREFERRED EMBODIMENT

Figure 1:
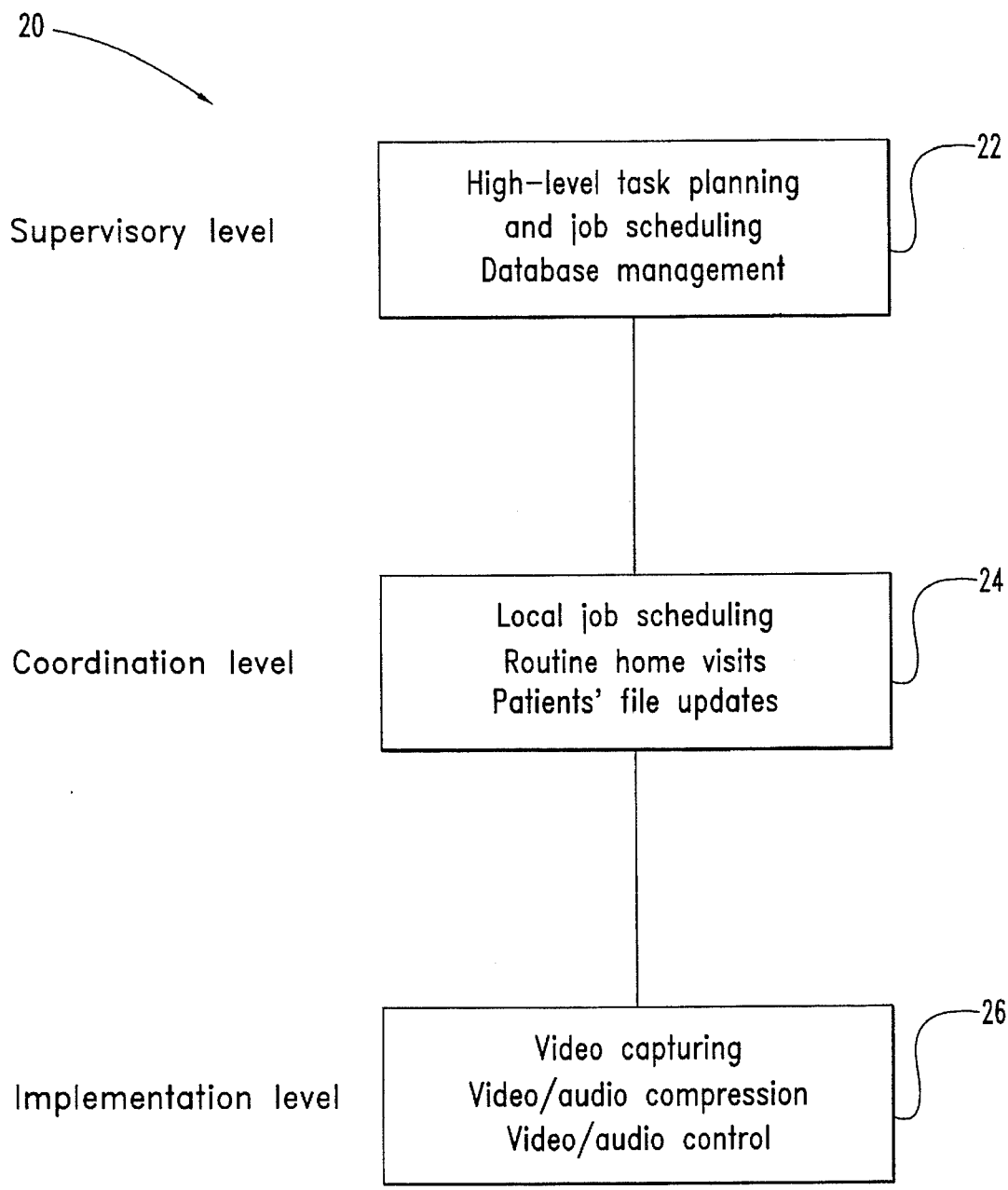
FIG. 1 is a block diagram of the system hierarchy in accordance with the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, the overall system hierarchy 20, in accordance with a preferred embodiment of the present invention, is shown. The overall system includes three subsystems: (1) a Supervisory level consisting of a Supervisory Control Center (SCC) 22; (2) a coordination level consisting of a number of remote Master Monitoring Stations (MMS) 24; and (3) an implementation level consisting of a number of Slave Monitoring Stations (SMS) 26. In operation, the SCC 22 functions as a central command station to oversee the operation of the individual monitoring centers by performing, among other duties, on-line task planning, such as specific home health care treatment for the multiplicity of patients requiring care, database management and job scheduling, such as assigning appropriate health care providers to particular patients requiring "in-home" visits. At the various MMS's 24, health care providers, such as nurses, physicians and other health care professionals, perform "in-home" visits, dispatched by SCC, through visual and audio communications over telephone lines as will be more fully discussed hereinafter, perform local job scheduling, and maintain and update the patient's files. The SMS's 26 are located within the various patient's homes and are linked to a particular MMS 24 during an "in-home" visit by a health professional. As will be more fully discussed hereinafter, the SMS 26 performs on-line video/audio acquisition and communications, signal processing, such as video/audio (de)compression, and camera selection/control during an "in-home" visit.

Figure 2:
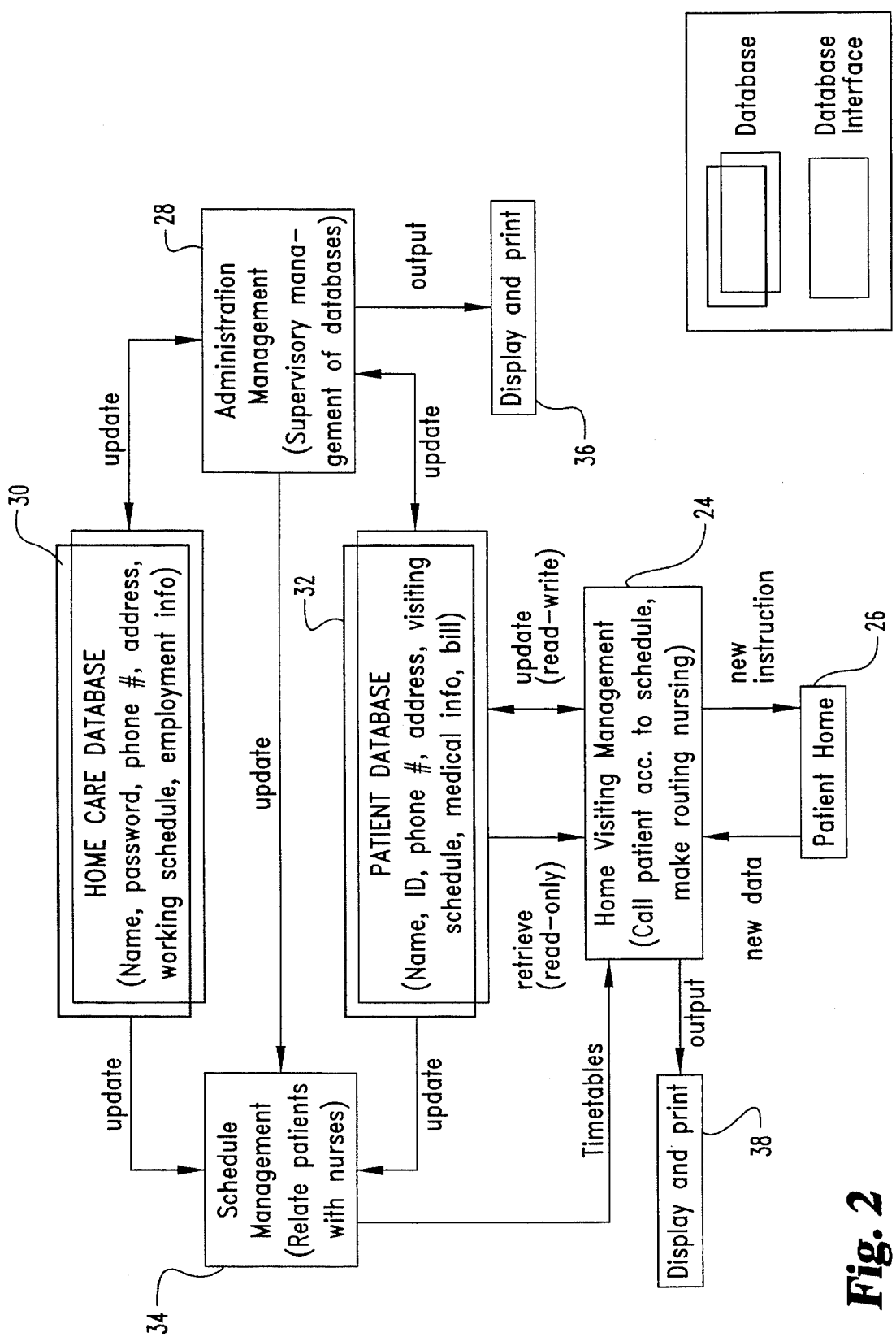
FIG. 2 is a flow chart showing the routes of information exchange within the system of the present invention.

Referring now to FIG. 2, information exchange routes within the system of FIG. 1 are shown. The system includes two main databases which should permit on-line data storage/retrieval and updating during multimedia data communications. In a preferred embodiment, the databases are relational databases. The first is a home care database 30 which includes data relating to the various health care professionals that perform "in-home" visits via the MMS's 24. The home care database 30 includes, for example, the names, passwords, telephone numbers, addresses, working schedules and other employment information of the various health care professionals. This information permits the health care professionals to access the system and further permits the Administration Management 28 and Schedule Management 34 portions of the SCC 22 to supervise and schedule jobs for the health care professionals. The Administration Management portion 28 may access and update the home care database 30 while the Schedule Management portion may only access information from the database 30.

The second database is the patient database 32 which contains medical data for the multiplicity of patients requiring home health care. For each patient, the patient database may include, for example, the patient's name, identification number, telephone number, address, in-home visiting schedule, billing information and medical information. In a preferred embodiment, as will be more fully discussed hereinafter, the patient database 32 contains multimedia data relating to each patient. In operation, the Administration Management portion 28 of the SCC 22 may access and update the patient database while the Schedule Management portion may only access patient information from the database 32. In addition to the SCC 22, the various home health care professionals may both access and update the patient database 32 via the MMS's 24.

In addition to accessing and updating the nurse 30 and patient 32 databases, the Administration Management portion 28 of the SCC 22 may also oversee and update the Schedule Management portion 34 as well as display and retrieve any accessible information via output 36. Similarly, the home health care professional may display and print information from the patient database 32 from an MMS 24 via output 38. Finally, the MMS 24 may access the Schedule Management portion 34 of the SCC 22 to retrieve scheduling information, and may further be linked to any one of the multiplicity of SMS's 26 via telephone communications for communication therebetween.

Figure 3:
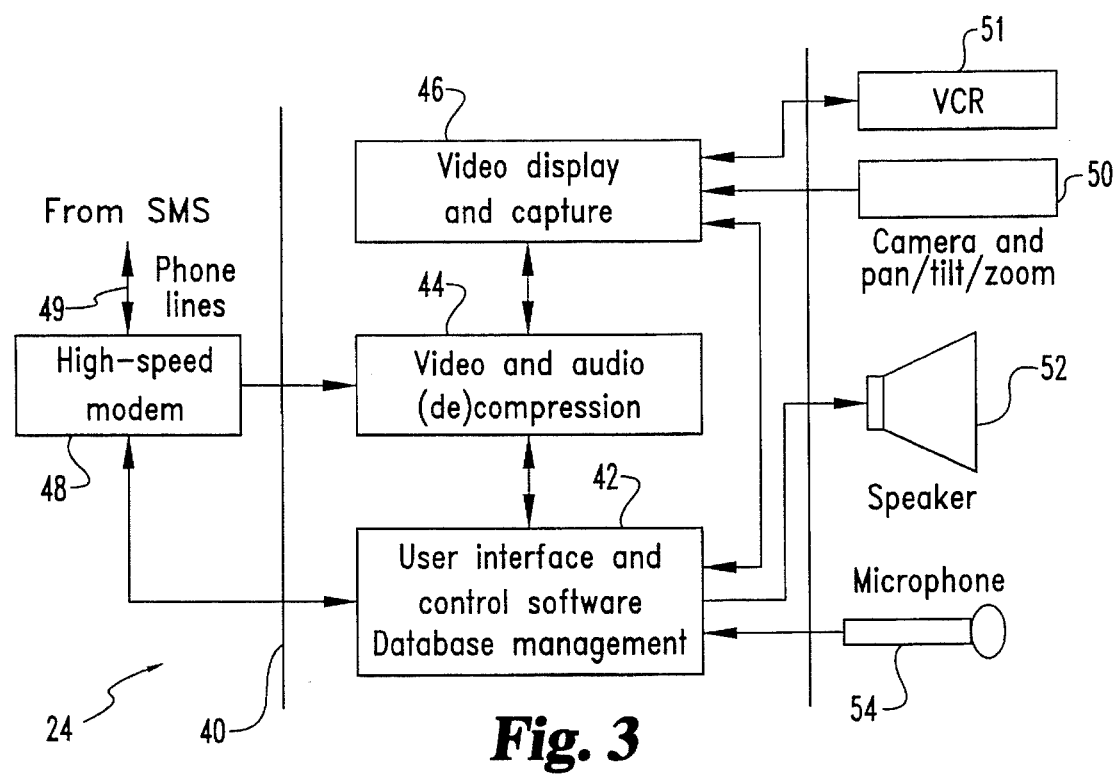
FIG. 3 is a block diagram representation of a master monitoring station in accordance with the present invention.

Referring now to FIG. 3, a preferred embodiment of MMS 24 is shown. MMS 24 includes, as its central component, a computer 40. Preferably, computer 40 is a 486-DX66 personal computer (PC), although the present invention contemplates using alternative computers having at least the capabilities of a 486-DX66 PC. Several application specific modifications have been made to computer 40 in accordance with the present invention. For example, computer 40 includes a video capture and display portion 46 coupled to a camera 50 having pan, tilt and zoom capabilities, and a video cassette recorder (VCR) 51. Video capture and display portion 46 is also coupled to video and audio (de)compression portion 44 which receives multimedia data through telephone lines 49 via high-speed modem 48. Video and audio (de)compression portion 44, as well as high-speed modem 48, are further coupled to user interface and control software database management portion 42 for controlling the multimedia data communicated via modem 48. The user interface portion 42 is, in a preferred embodiment, a windows-based interface which will be more fully discussed hereinafter. User interface and control software database management portion 42 is further connected to a speaker 52 and microphone 54, as well as video display and capture portion 46.

Figure 4:
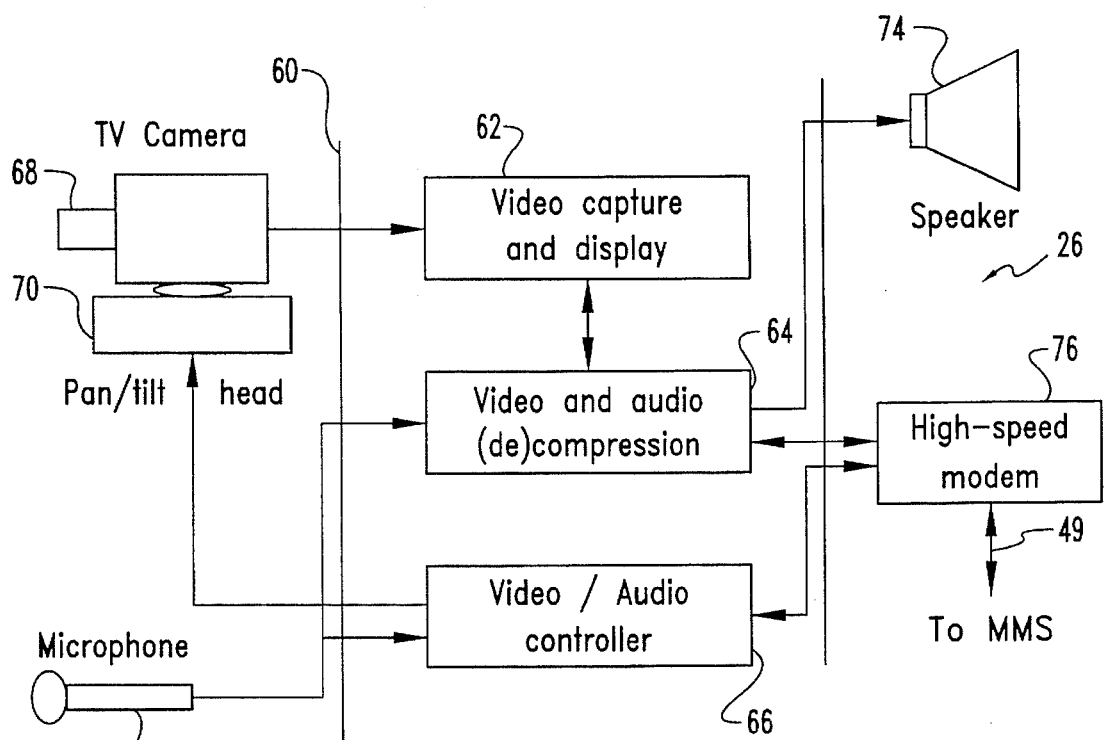
FIG. 4 is a block diagram representation of a slave monitoring station in accordance with the present invention.

Referring now to FIG. 4, a preferred embodiment of SMS 26 is shown. As with MMS 24, SMS 26 has, as its central component, computer 60. Preferably, computer 60 is a 486-DX66, although the present invention contemplates using other PC's having at least the capabilities of a 486-DX66. Computer 60 includes a video capture and display portion 62, including a monitor, connected to an external video camera 68 and video and audio (de)compression portion 64. Preferably, video and audio (de)compression portion 64 is identical to video and audio (de)compression portion 44 of FIG. 3. Video and audio (de)compression portion 64 is, in turn, connected to an external microphone 72, speaker 74 and high-speed modem 76. Preferably, high-speed modem 76, connectable to a telephone line 49, is identical to modem 48. Finally, computer 60 includes a video/audio controller section 66 connected to an external pan/tilt head 70 which is, in turn, connected to video camera 68. Video/audio controller 66 controls the video camera 68 for panning either left or right, or tilting either up or down. In a preferred embodiment, video camera 68 further includes a lens capable of increasing magnification and decreasing magnification to thereby provide a zoom in and zoom out feature. Video/audio controller 66 is further connected to one or more microphones 72 associated with the camera 68 for processing the audio signals received therefrom. Audio processing may include, for example, controlling microphone sensitivity, filtering out background noise and electronically enhancing the audio signals.

In operation, MMS 24 is located within a health care facility such as, for example, a hospital, physician's office, or other health care professional's place of business, and SMS 26 is located within the home of a patient requiring in-home health care. When, according to scheduling information received from SCC 22, a health care professional is scheduled to perform an "in home" visit to a particular patient, the health care professional links the MMS 24 modem 48 to the patient's SMS 26 modem via ordinary telephone lines, by known methods, to establish a communications link therebetween. In accordance with the user interface and control software portion 42 of computer 40, the health care professional may activate the video camera 68 features, such as pan left, pan right, tilt up, tilt down, zoom in or zoom out, to view various areas of the patient's home. The health care professional may further control the processing of the audio signals received via the various microphones 72. In so doing, video camera control signals and audio control signals, corresponding to operator commands via the user interface, are supplied to modem 48 by the control software portion 42 of computer 40. The video/audio control signals are transmitted over the telephone link to modem 76 of SMS 26 where video/audio controller portion 66 of computer 60 receives the signals and actuates the video camera 68 via pan/tilt head 70, and controls the audio signals from the various microphones 72 via known methods.

The video signals produced by video camera 68 are captured by video capture portion 62. The captured video signals, as well as audio signals provided by the various microphones 72 associated with the video camera 68, are compressed by video and audio (de)compression portion 64 and transmitted, via modem 76, to modem 48 of MMS 24. These video and audio signals are then decompressed within video and audio decompression portion 44 of computer 40, the decompressed video signals are displayed on a monitor by video display portion 46, and the decompressed audio signals are reproduced by speaker 52. In this way, the health care professional may visually search various areas, and listen to audible sounds generated, within a patient's home and in real-time by providing appropriate operator commands to the user interface portion 42 of MMS computer 40. This multimedia data may further be stored, in real-time, within the database management portion 42 of computer 40 and/or recorded on VCR 51.

While the health care professional is observing the real-time multimedia data transmitted to MMS 24, the patient may similarly observe multimedia data related to, or provided by, the health care professional. To this end, camera 50 may provide video signals corresponding to real-time images of the health care professional to video capture portion 46 of computer 40. Alternatively, the health care professional may provide video signals corresponding to a prerecorded video segment to video capture portion 46 via VCR 51. Additionally, the microphone 54 may be used to provide real-time audio signals corresponding to the health care professional's voice to control software portion 42. Alternatively, the health care professional may provide a prerecorded message, such as an announcement, or music, for example, to control software portion 42. In any event, the video and audio data is compressed by video and audio (de)compression portion 44, and sent through the control software portion 42 to modem 48 for transmission to modem 76 of SMS 26 via the telephone link.

The multimedia data relating to, or provided by, the health care professional is received by modem 76 and decompressed by video and audio (de)compression portion 64 of computer 60. The decompressed video signal is then displayed on a monitor by video display portion 62, and the decompressed audio signal is reproduced at the speaker 74. In this way, the patient may observe, in real-time, multimedia data relating to, or provided by, the health care professional.

The foregoing system may be used by a health care professional to provide an "in-home" visit to a patient in need of health care from a remote location. At all times, the health care professional may control the video camera functions to view any visually accessible location within the patient's home in real-time, and may further hear audible sounds created within the patient's home, also in real time. Simultaneously, the patient may both see and hear either the health care professional in real-time, or see and hear information provided by the health care professional. In this way, a real-time "in-home" visit may be conducted to provide many aspects of health care for a patient including one-on-one communication, medical counseling, educational sessions and instructional demonstrations, to name a few.

The foregoing system may further be used to provide a continuous, or full-time, in-home monitor of the patient's condition and/or activities. The MMS 24 may thus be operated to monitor the multimedia data transmission relating to the patient, in real time, and alert the patient and/or the health care professional to the occurrence of certain predetermined events or conditions detected within the multimedia data. For example, the MMS 24 may be operated to monitor patient compliance with medical treatment such as taking medication, performing prescribed routines, abstaining from ingesting certain foods, beverages and medications, abstaining from certain physical activities and the like. The MMS 24 may also be operated to monitor lack of patient activity to alert the health care professional to patient injury, unconsciousness and death. Finally, the MMS 24 may be operated to monitor the multimedia patient data for a distress signal provided by the patient, such as through a predetermined voice command or pattern, or via a predetermined electrical signal transmitted by the patient. In any event, the patient and/or health care professional may be alerted to the detection of the predetermined event or condition by providing an audio prompt, or by automatically placing a telephone call to the appropriate party, for example.

In a preferred embodiment, the video and audio (de)compression portions 44 and 64 of computers 40 and 60 respectively, are ShareVision PC3000 desktop video conferencing system boards, manufactured by Creative Labs, Inc. The color video board contains two composite (NTSC or PAL) inputs and one S-video input. Using a vector adaptive transform processing (VATP) compression algorithm and a high speed computer modem, such a 28.8 Kbps modem supplied by ShareVision, the frame rate is capable of reaching up to 7–15 frames per second at 96×80 pixels, at up to 24 bits per pixel. Image resolution and corresponding color bits are user selectable in real time. High resolution still images with 320×240 pixel resolution at up to 24 color bits per pixel can be captured using a "snapshot" function. The audio board has tow outputs and one input with a bandwidth of 4800 bps dynamically allocated.

Preferably, a CCD camera is used for either video camera 50 or 68, although such cameras, as well as motorized zooms, may be cost prohibitive. It has been found through experimentation that compact camcorders with built-in remote controllable zooming are presently more reasonably priced and provide acceptable alternatives in most cases. A Sunpack camera pan/tilt head with infrared remote controller, manufactured in Japan, is preferably used as the video camera pan/tilt head 70. The control of the camera head is accomplished by using computer parallel ports and modifying the original infrared remote controller such that an analog switch can be controlled by the PC to simulate the control buttons on the remote controller. The control software portion 42 of computer 40 contains software algorithms for controlling the video camera pan/tilt/zoom movements via operator commands. The microphones, speakers and VCR may be any of a variety of known components and will therefore not be discussed further.

Thus far, the system of the present invention has been described as having a single video camera 68 located within a patient's home. However, since most homes have multiple rooms, it is desirable to have multiple video cameras located throughout a patient's home. In some situations, at least one video camera will be located in each room of the patient's home, and in other situations, depending on the patient and the health care professional, video cameras need only be located in selected rooms. In any event, the present invention contemplates locating multiple video cameras within any given patient's home.

Figure 5:
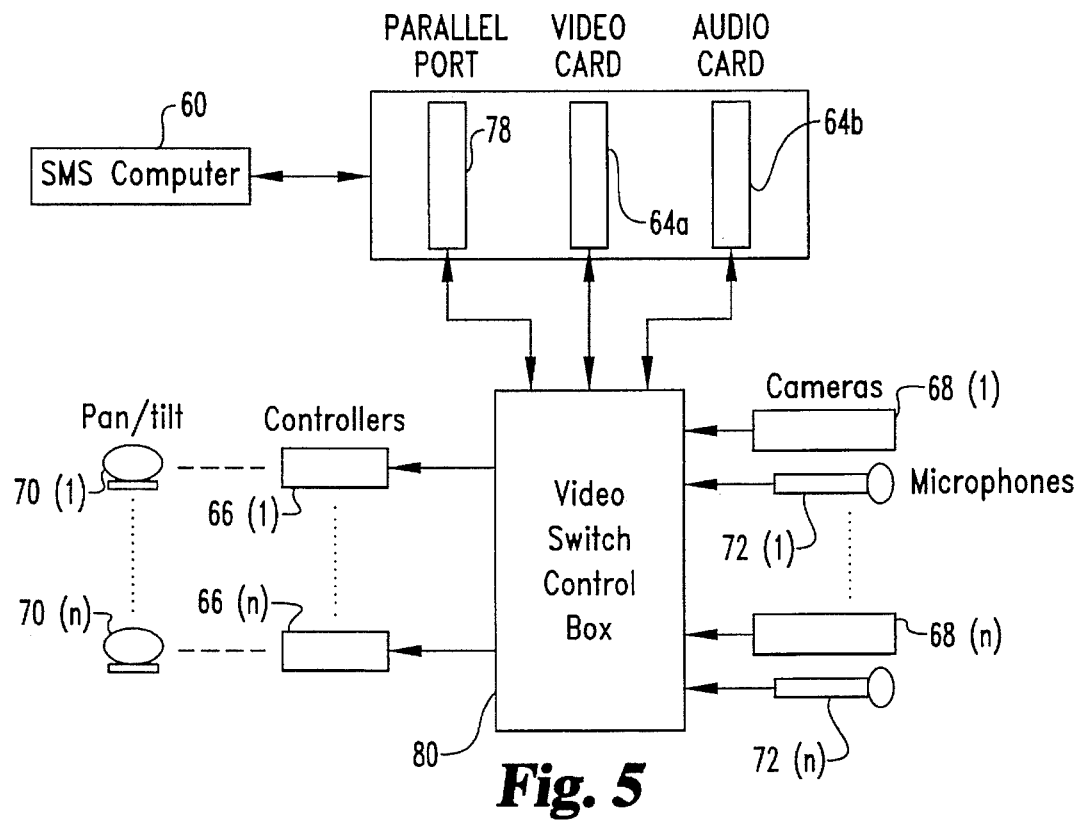
FIG. 5 is a block diagram representation of a multi-camera interface to the slave monitoring station of FIG. 4.

Referring now to FIG. 5, a block diagram circuit is shown connected to SMS computer 60 for controlling the switching between video cameras located in the various rooms of a patient's home. A video switch control box 80 is connected to a parallel port 78 of SMS computer 60, as well as to the video and audio boards 64a and 64b respectively of video and audio (de)compression portion 64. The variable number of video cameras 68(*l*)–68(*n*), corresponding microphones 73(*l*)–72(*n*), camera controllers 66(*l*)–66(*n*) and pan/tilt heads 70(*l*)–70(*n*) are also connected to the video switch control box 80. The user interface and control software portion 42 of computer 40 permits a health care professional to issue operator commands, in a manner to be more fully discussed hereinafter, to choose a desired video camera 68 and corresponding microphones 72 for receiving multimedia data therefrom. Video switch control box 80 is a video multiplexing circuit which may be of known design and preferably based upon any of a variety of known and commercially available video multiplexer integrated circuits.

Figure 6:
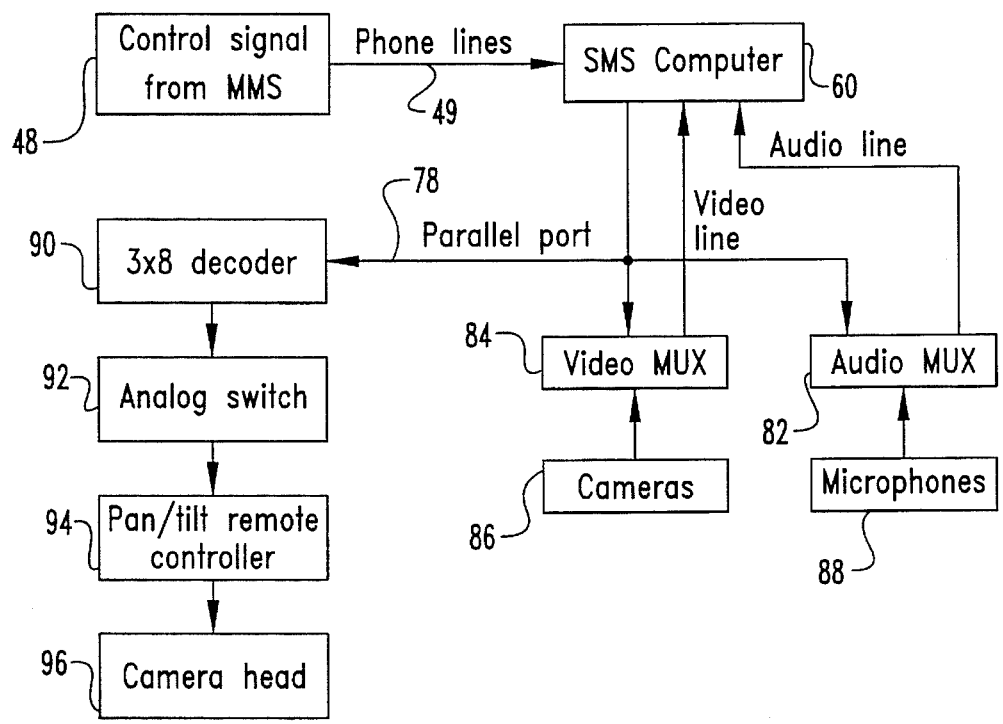
FIG. 6 is a block diagram representation of a video camera control system for use with the slave monitoring station of FIG. 4.

Referring now to FIG. 6, a specific example of video camera switching and pan/tilt/zoom control interface circuitry is shown for a system having eight video cameras located within a patient's home. It is to be understood, however, that the present invention contemplates using more than eight video cameras and those skilled in the art will recognize that the expansion of such a system is a straightforward application of the principles discussed herein. MMS modem 48 is coupled to SMS computer 60 via telephone link 49 so that SMS computer 60 may receive control signals from the MMS computer 40 as previously discussed. The video and audio (de)compression portion 64 of SMS computer 60 is connected via video multiplexer 84 to a plurality of video cameras 86 located within a patient's home, and is connected via audio multiplexer 82 to a corresponding plurality of microphones 88 located proximate to video cameras 86. Each pan/tilt head 96 is connected to a pan/tilt remote controller 94 which, in turn is connected to an analog switch 92. The analog switch of each of the eight video cameras are connected to a 3×8 decoder which, in turn is connected to video multiplexer 84, audio multiplexer 82 and to the parallel port 78 of computer 60. As previously discussed, video switching control is accomplished through the parallel port 78 of computer 60 through video multiplexer 84. Through the use of operator commands provided by the health care professional at MMS computer 40, a desired video camera and corresponding microphone located within the patient's home may be selected for monitoring a particular location. Pan/tilt/zoom commands provided by the health care professional at MMS computer 40 are routed through the 3×8 decoder to the appropriate video camera to thereby actuate the desired camera functions.

Figure 7:
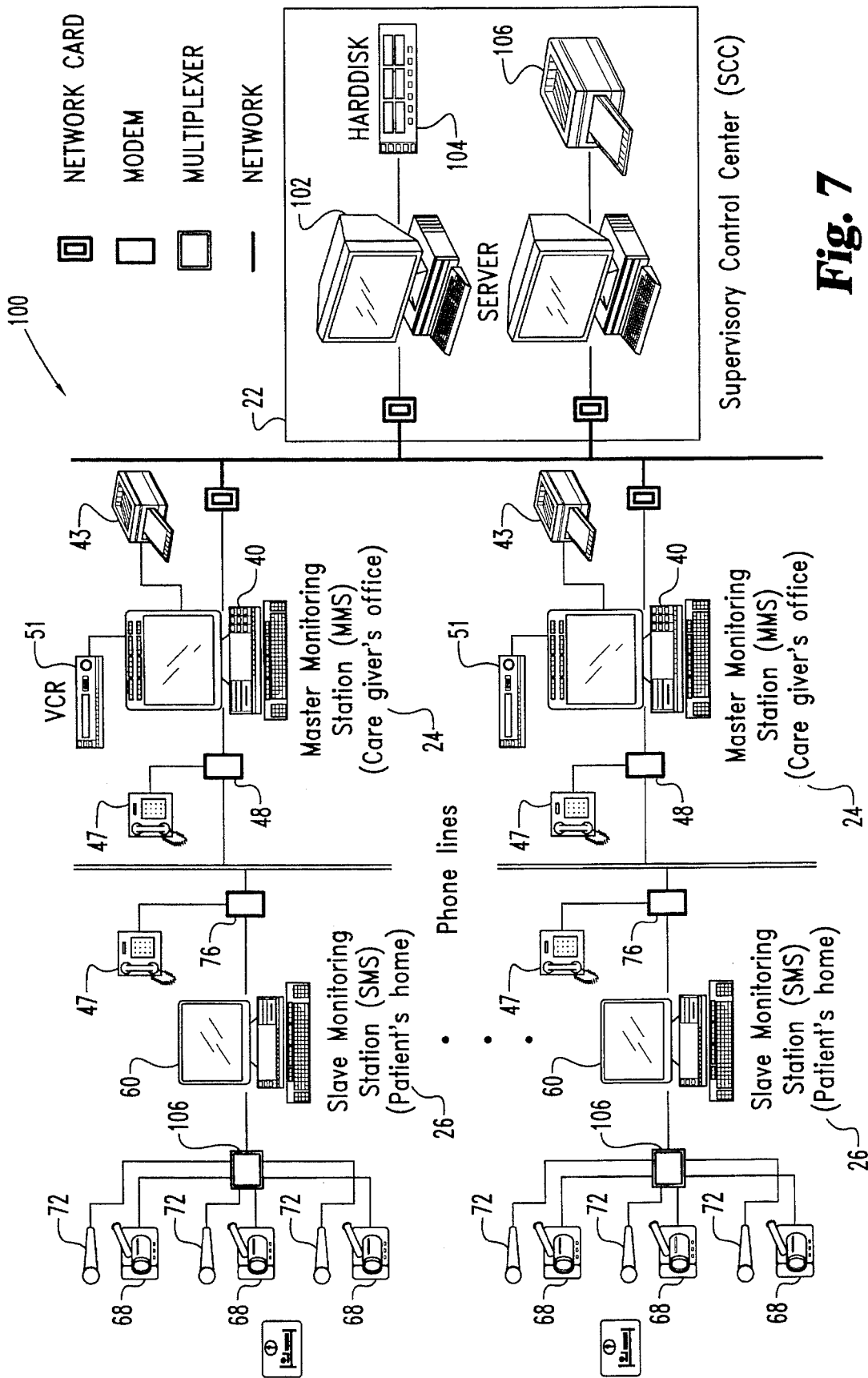
FIG. 7 is a diagrammatic illustration of a remote visual monitoring system in accordance with the present invention.

Referring now to FIG. 7, a remote visual monitoring system 100 in accordance with the present invention is shown. Within the SCC 22, high-level task planning and job scheduling are performed off-line based on actual demand, priority of visits and resources available. A computer 102 within SCC 22 is connected via a local area network to a main computer (not shown) where global databases including patient, health care professional, health care company and health insurance data are maintained. Computer 102 is further connected to a number of MMS computers 40. In a preferred embodiment, computer 102 is a 486-DX2/66 PC, although the present invention contemplates using other computers having at least the capability of a 486-DX2/66 PC. A harddisk 104, or the like, is located within the SCC 22 for maintaining the patient and health care professional databases previously discussed. A printer 106 is also provided for generating hard copies of any data accessible by the computer 102.

SCC 22 communicates with a number of MMS's 24 through a server/client network scheme. The various MMS's 24, on the other hand, communicate with each other via a peer-to-peer network, or information sharing group, in order to exchange information with each other in a secured and integrated manner. Each MMS 24 may include a computer 40, telephone 47, telephone modem 48, VCR 51, and printer 43. At the MMS 24 level, local job scheduling is performed based on the tasks dispatched by SCC 22, and on the priority of visits. A patient manager or other health care professional may conduct routine visits to a patient via the previously discussed visual monitoring system. The patient manager can also record results and update patient data as needed. The patient manager may further coordinate the patient and his/her physicians for further visits when necessary.

An MMS 24 may communicate with a number of SMS's 26 each of which is located within a separate patient's home. Each SMS 26 may include a computer 60, telephone 47, telephone modem 76, video multiplexer 106, and a plurality of video cameras 68 and corresponding microphones 72. It is to be understood that all hardware and software previously discussed and necessary to provide video camera switching and pan/tilt/zoom functions are incorporated into this diagram, although not specifically shown for ease of illustration. At the SMS 26 level, video capturing, video/audio processing and communications are carried out by previously discussed hardware and software and their interfacing components.

User interfaces are an important aspect of the present invention and play a key role in the operation of MMS 24. In order to reduce the requirements of extensive training for users, a windows-based user interface environment is used to translate operator commands to the appropriate control signals usable by the remote visual monitoring system 100. One user interface, as fully discussed hereinafter with respect to FIGS. 8–22, was developed using Microsoft Access™. The user of MMS 24 is assumed to have basic knowledge of windows/DOS operations and the user interface of the present invention is generally self explanatory. As has become commonplace in the windows environment, an on-line help system is available during operation of the user interface.

Figure 8:
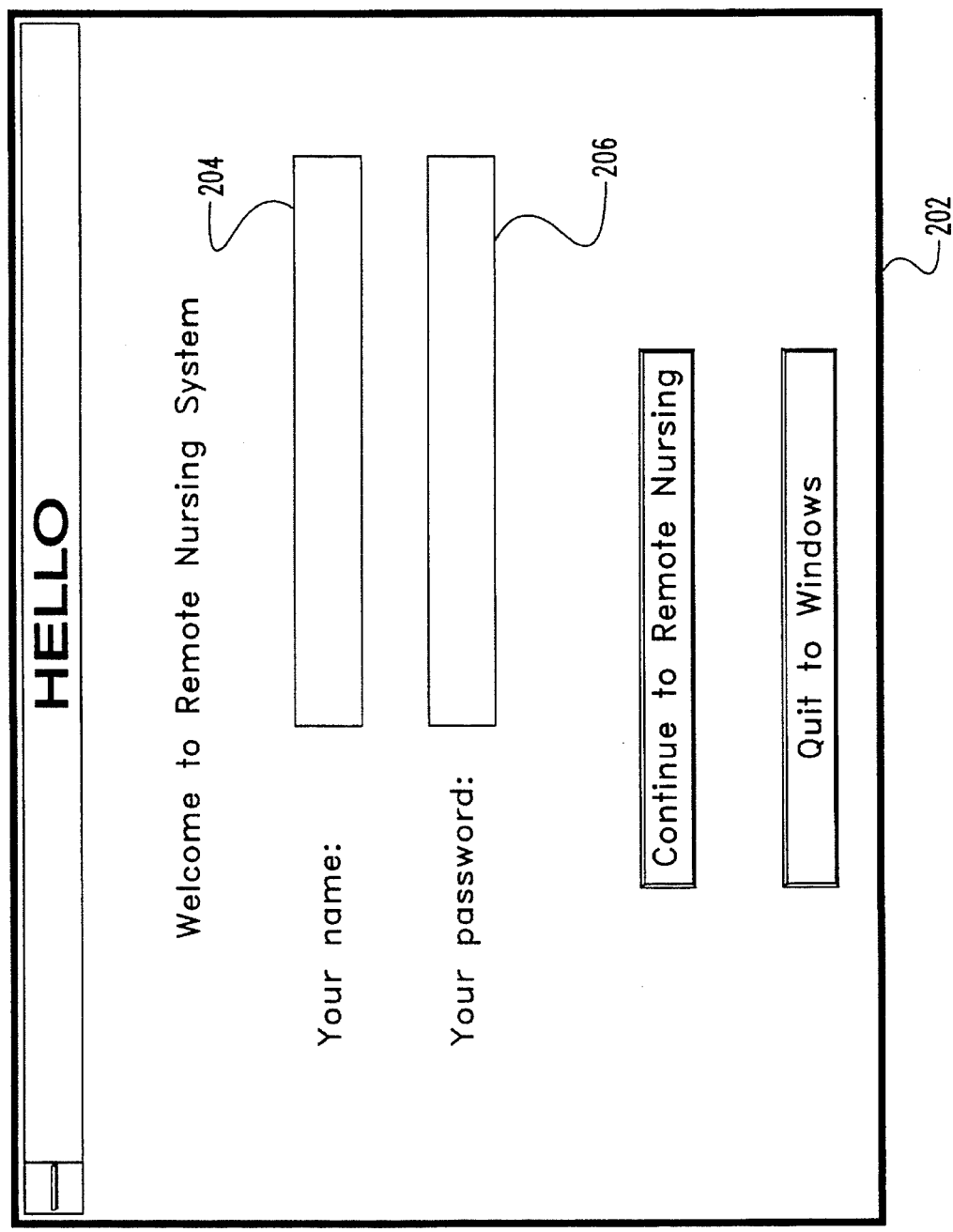
FIG. 8 is a graphical representation of a log-in screen for a windows-based user interface software program, for use with the remote visual monitoring system of FIG. 7, in accordance with another aspect of the present invention.

Referring now to FIG. 8, a log on screen 202 for the user interface of the present invention is shown. The screen 202 requires a health care professional operating an MMS 24 to enter their name 204 and corresponding password 206. Screen 202 thus acts as a security measure by ensuring that only legitimate users may operate the system.

Figure 9:
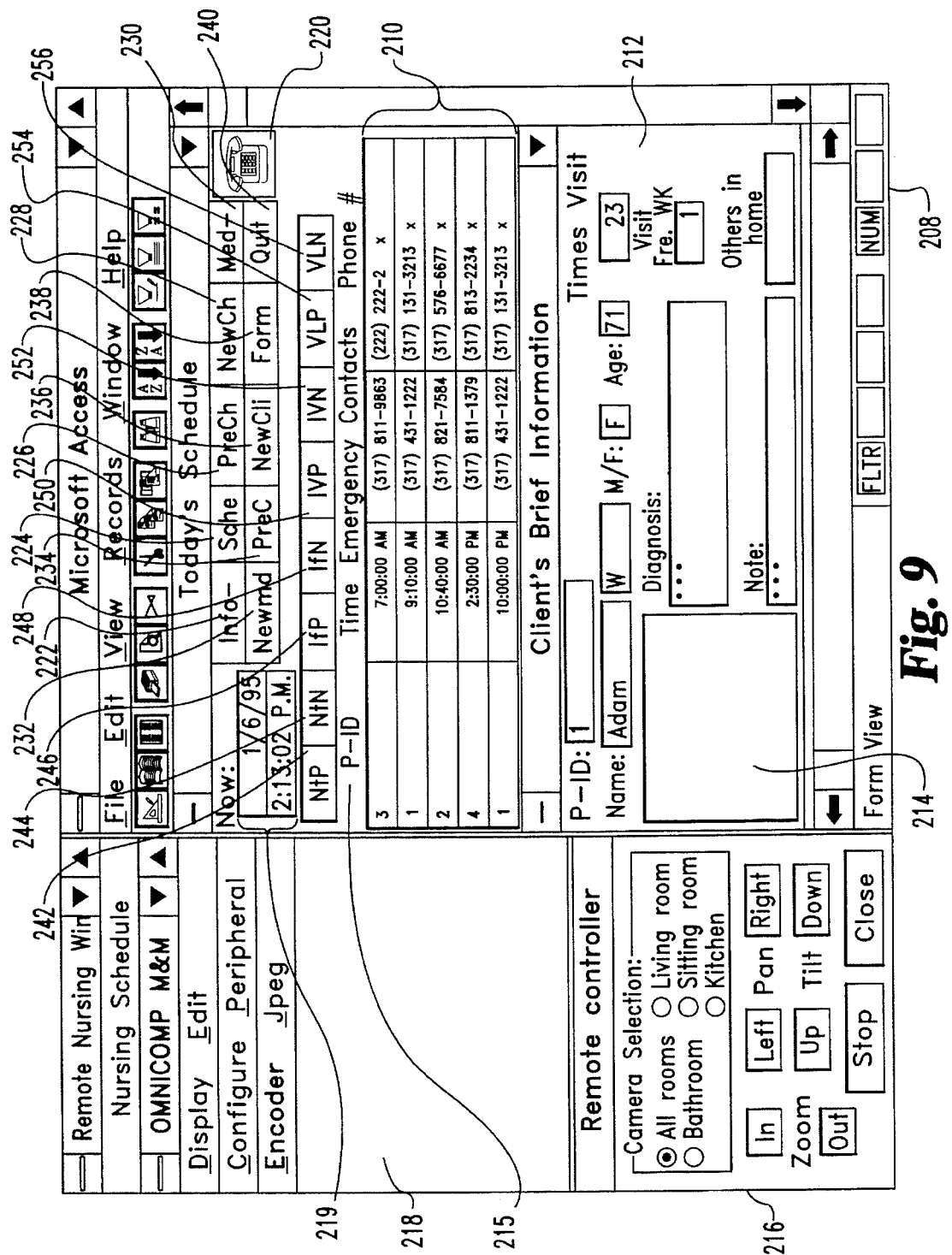
FIG. 9 is a graphical representation of the initial patient list screen of the user interface program.

Referring now to FIG. 9, the initial screen 208 containing a list 210 of patients scheduled to be visited, via the system 100, for the present day follows the log on screen 202. In the lower portion 212 of the window, brief information relating to the patient, which corresponds to a selected patient identification number 215 highlighted within the patient list, is provided. The brief patient information may include any of the items contained within the patient's detailed information file, which will be more fully discussed hereinafter with respect to FIG. 11, such as the patient's photo 214 for example. The current date and time 219 appear above the upper left corner of the list of patients 210, and a control panel 216 for controlling video/audio information generated from within a patient's home appears at the lower left portion of the screen. When contact is established with a patient during a home visit, conducted via system 100, the health care professional may operate the control panel 216, in a manner to be more fully discussed hereinafter, such that the real-time image of selected areas within the patient's home may be viewed within display portion 218. Finally, several user interface options 220–240 are available within this application and each are discussed separately below.

Figure 10:
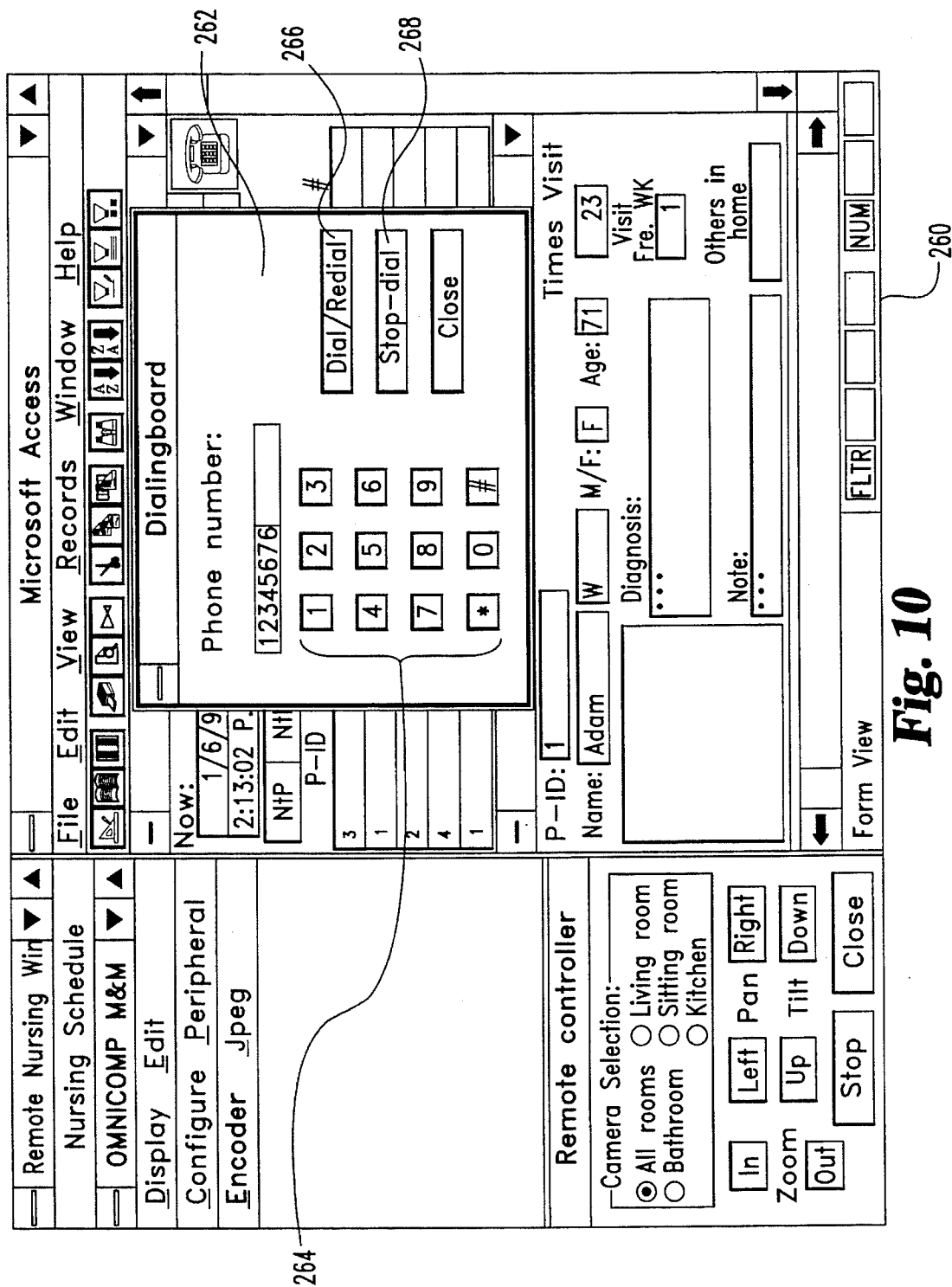
FIG. 10 is a graphical representation of a telephone dialing option within the user interface program.

By choosing the telephone option 220, the program automatically dials the telephone number of the patient highlighted in the patient list to thereby link MMS 24 with that particular patient's SMS 26. If the patient's telephone number is not known, or if it is incorrect within the automatic dialing routine such that the MMS 24 is unable to connect with a known SMS 26, a manual dialing screen 260 containing a "Dialingboard" mini screen 262 appears with a telephone dialing pad 264 incorporated therein as shown in FIG. 10. By selecting the dial/redial option 266, selecting the appropriate numbers, and then selecting the stop-dial option 268, a telephone number may be "manually" dialed by MMS 24 to establish a computer link with the appropriate SMS 26.

Figure 11:
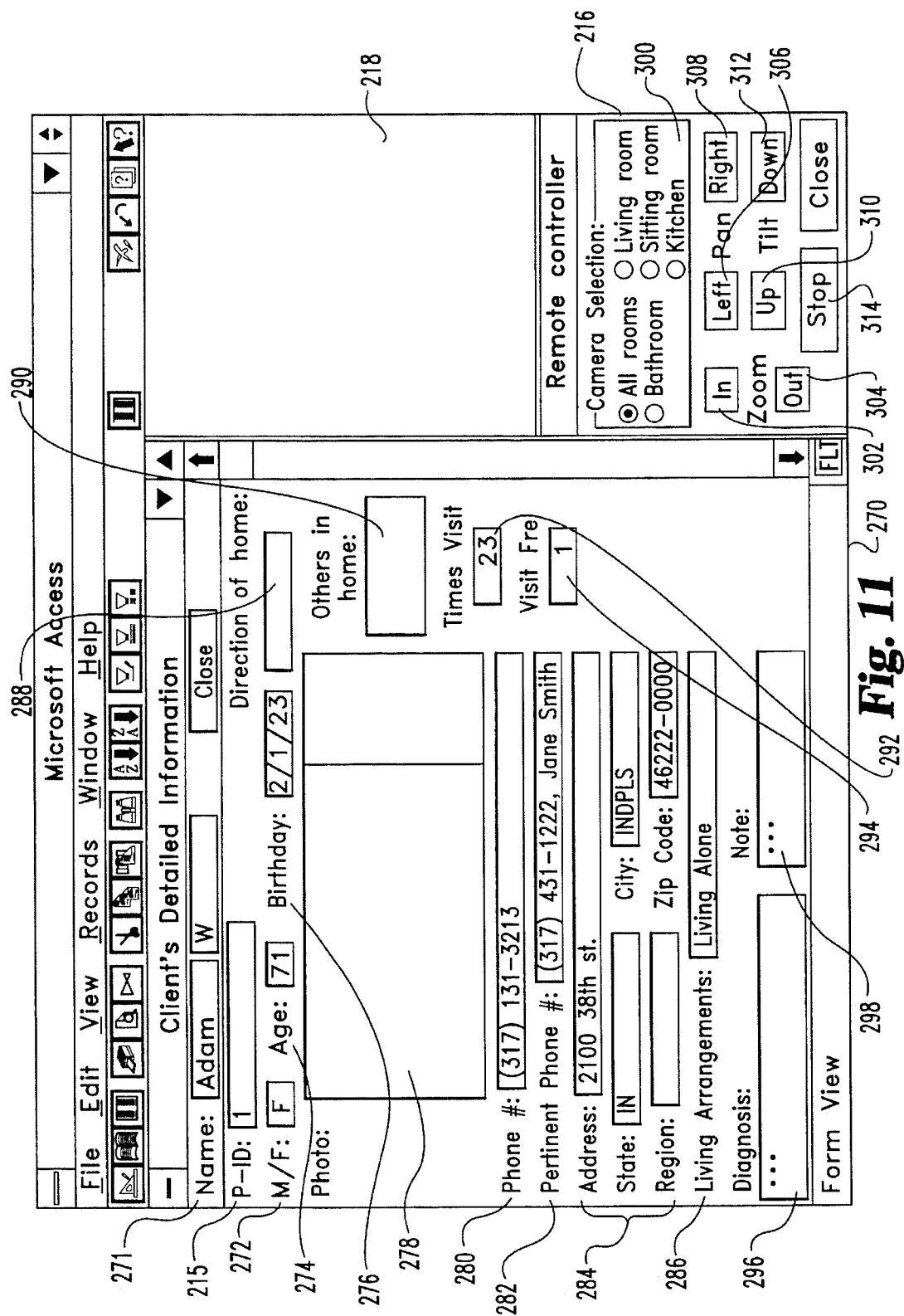
FIG. 11 is a graphical representation of a Client's Detailed Information option within the user interface program.

Referring back to FIG. 9, once a telephone link is established with the patient whose patient identification number 215 was selected by the health care professional, the health care professional has several screen options with which to conduct the "in-home" visit. The first is the "Info-" option 222 which is shown in detail in FIG. 11. Referring to FIG. 11, the Client's Detailed Information screen 270 includes personal information about the client 215 including, for example, the client's (patient's) name 271, sex 272, age 274, birthday 276, phone number 280, address 284, living arrangements 286, direction of home 288, names of others living with the client 290, a still photo of the client 278 and a phone number 280 of a relative, guardian, trustee or the like. Certain medical information regarding the client may also be included within the screen 270 such as, for example, number of times that an "in-home" visit has been conducted to date 292, frequency of visits 294, patient diagnosis 296 and other notes of interest or importance 298.

A real-time video viewing portion 218 for viewing through the selected one of the plurality of video cameras located within the patient's home is included with screen 270, as well as all other screens used in conducting an "in-home visit". An audio/video control portion 216 is provided for choosing the room, and corresponding video camera, to view within viewing portion 218. Although not shown in any of the FIGS., the present invention contemplates that the control portion 216 may further include audio control functions to provide control over the microphones associated with each camera. Such control may include, for example, a muting function, volume/sensitivity adjustments, signal enhancement, and/or background noise filtering options.

The audio/video control portion 216 includes a camera selection portion 300 which permits the health care professional to choose a video camera, and associated microphones, from a variety of cameras for displaying the real-time image thereof within viewing portion 218. As previously discussed, the present invention contemplates locating one or more video cameras in as few as one, or as up to every, room within a patient's home. Thus, the camera selection portion 300 contains options for choosing a desired room to view such as, for example, a bedroom, living room, sitting room and kitchen. An "all rooms" option also exists which provides a plurality of smaller viewing screens within viewing portion 218 that permit the health care professional to view, in real-time, through all cameras within the patient's home at one time. Such an option is useful, for example, to facilitate the locating of the patient upon first establishing contact with SMS 26, and is therefore the default camera selection setting.

The audio/video control portion 216 further includes all video camera control features for controlling any one of the cameras located within the patient's home. The camera control features include zoom in 302, zoom out 304, pan left 306, pan right 308, tilt up 310 and tilt down 312. In operation, the user interface application may be configured such that the video control features 302–312 are actuated a predetermined amount for each selection of the corresponding feature. For example, a pan left selection may cause the appropriate camera to pan left approximately 5 viewing feet. Alternatively, the user interface application may be configured such that the video control features 302–312 are continuously actuated, upon selection thereof, until a stop 314 command is selected. For example, with this configuration, a pan left selection may cause the appropriate camera to pan left until the viewer selects the stop option 314.

Figure 12:
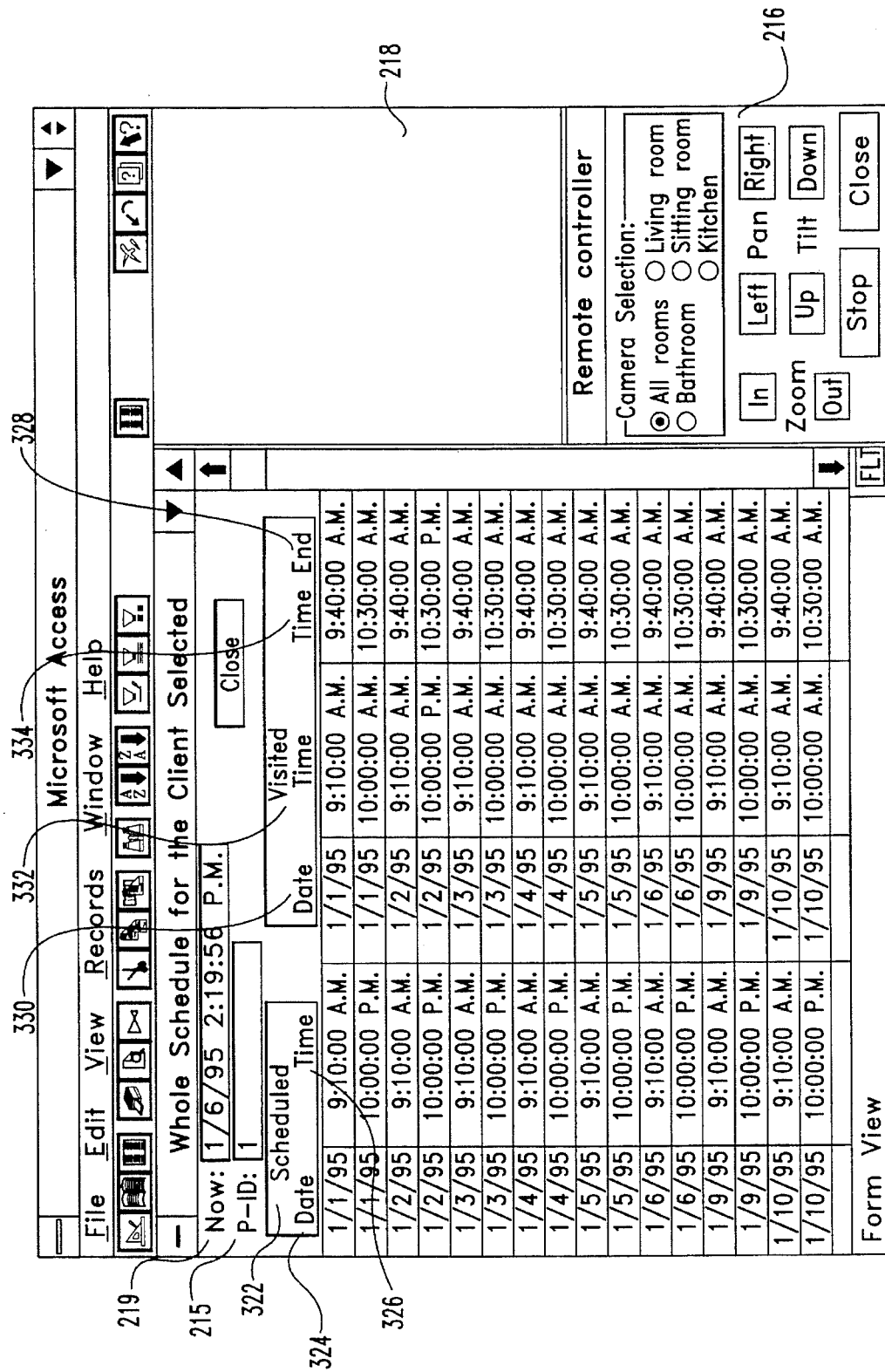
FIG. 12 is a graphical representation of a Client Scheduling option within the user interface program.

Referring briefly back to FIG. 9, a second option within an "in-home" visit is a patient schedule option 224 which provides a client schedule screen 320 as shown in FIG. 12. The right portions 216 and 218 of screen 320 are identical to screen 270 of FIG. 11 and will therefore not be discussed further. The date and time 219 and patient identification number 215 are included within the scheduling screen 320 for reference. The client schedule screen further includes a scheduling portion 322 which contains a list of dates 324 and times 326 for which an "in-home" visit is scheduled with that particular patient. The schedule portion may be updated or otherwise altered by the health care professional, by the health care professional's supervisor, or automatically via the Supervisory Control Center (FIGS. 1 and 7). A visitation log 328 is also provided which permits the health care professional to enter the date 330, start time 332 and ending time 334 of each visit conducted.

Figure 13:
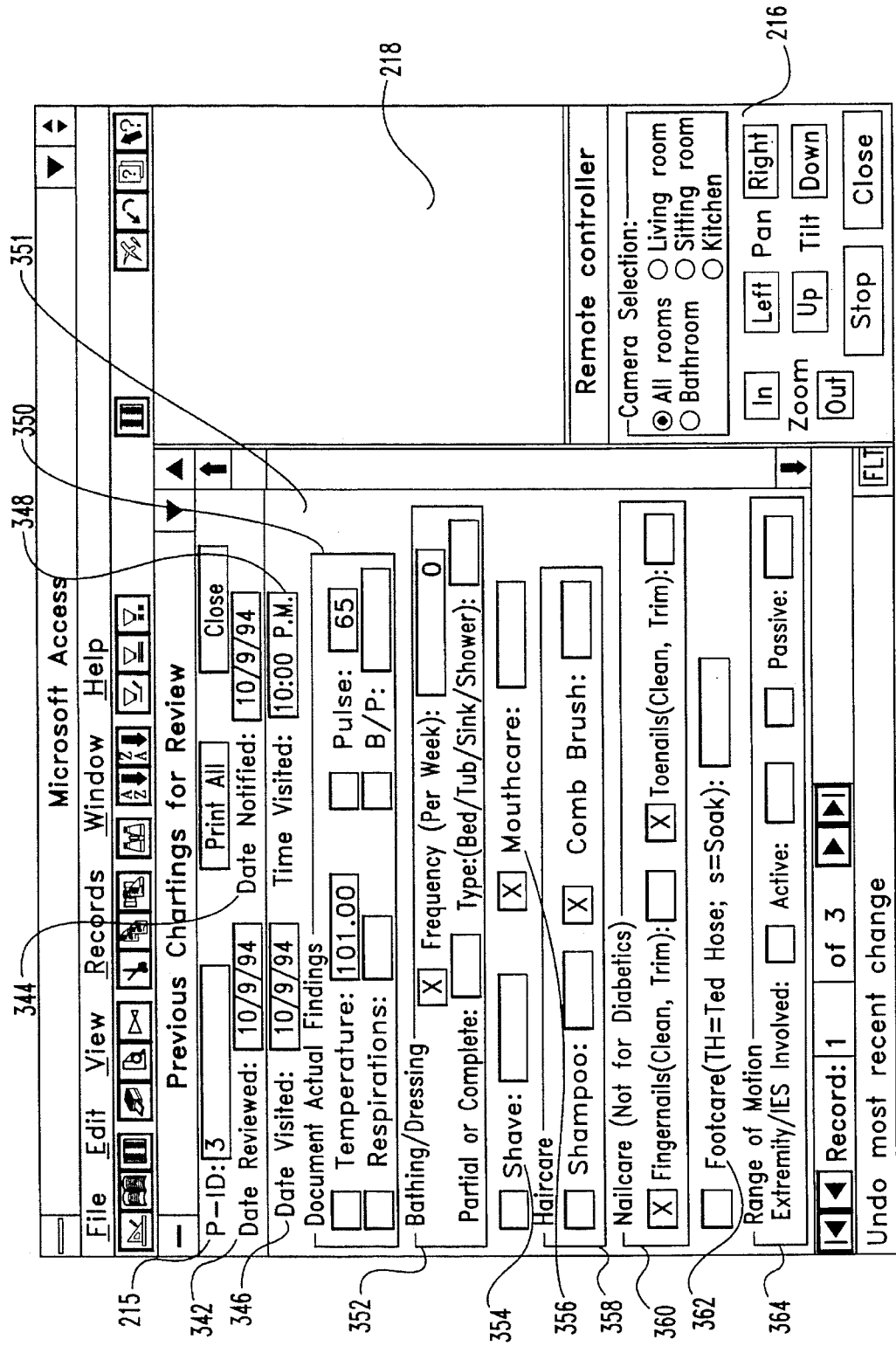
FIG. 13 is a graphical representation of a Charting Review option within the user interface program.

Referring again to FIG. 9, another option within an "in-home" visit is a "PreCh" option 226 which provides a "Previous Chartings" screen 340 as shown in FIG. 13. As with the previous screens, the right portions 216 and 218 are identical to screen 270 of FIG. 11 and will therefore not be discussed further. A previous chart 351 for the particular patient being visited contains identification information such as patient identification number 215 as well as the date 346 and time 348 that the visit was conducted. The chart 351 is intended to be reviewed, as part of a spot check or periodic review program, by the health care professional's supervisor. The chart 351 therefore contains information indicating the date of chart review 342 and date that the health care professional (Certified Home Health Aid, or CHHA) is notified of the review 348. The chart 351 further includes, as most clearly shown in its expanded form in FIG. 14, various instructional and training items that may be reviewed such as, for example, bathing/dressing 352, shaving 354, mouthcare 356, haircare 358, nailcare 360, footcare 362, range of motion 364, medication assistance 366, toileting 368, ambulation or transfer assistance 370, skin care 371, linen change 372, bed making 374, house keeping 376, meal preparation 380, dietary instructions 382, physical activities 384 and special procedure instructions 386. Actual findings 350 made by the visiting health care professional are also documented as part of the chart 351 such as, for example, temperature, pulse, respiration and blood pressure. The chart 351 further includes a portion of interest to the supervisor including such information as an indication to contact the health care professional for changes in the patient's condition or other problems 388, initials of the supervisor 390, the name of the health care professional providing the care 392 and any further notes to be made by the supervisor 394. The present invention further contemplates that the health care professional's signature 396 may be read into memory, as part of the home care database 30 (FIG. 2), and may thereafter be affixed to the chart 351.

Referring again to FIG. 9, another option within an "in-home" visit is a "NewCh" option 228 which provides a "New Chartings" screen (not shown). The new chartings screen is identical to screen 320 with the exception that it contains no patient or health care professional information. The new chartings screen is thus a blank form of screen 320.

Figure 15:
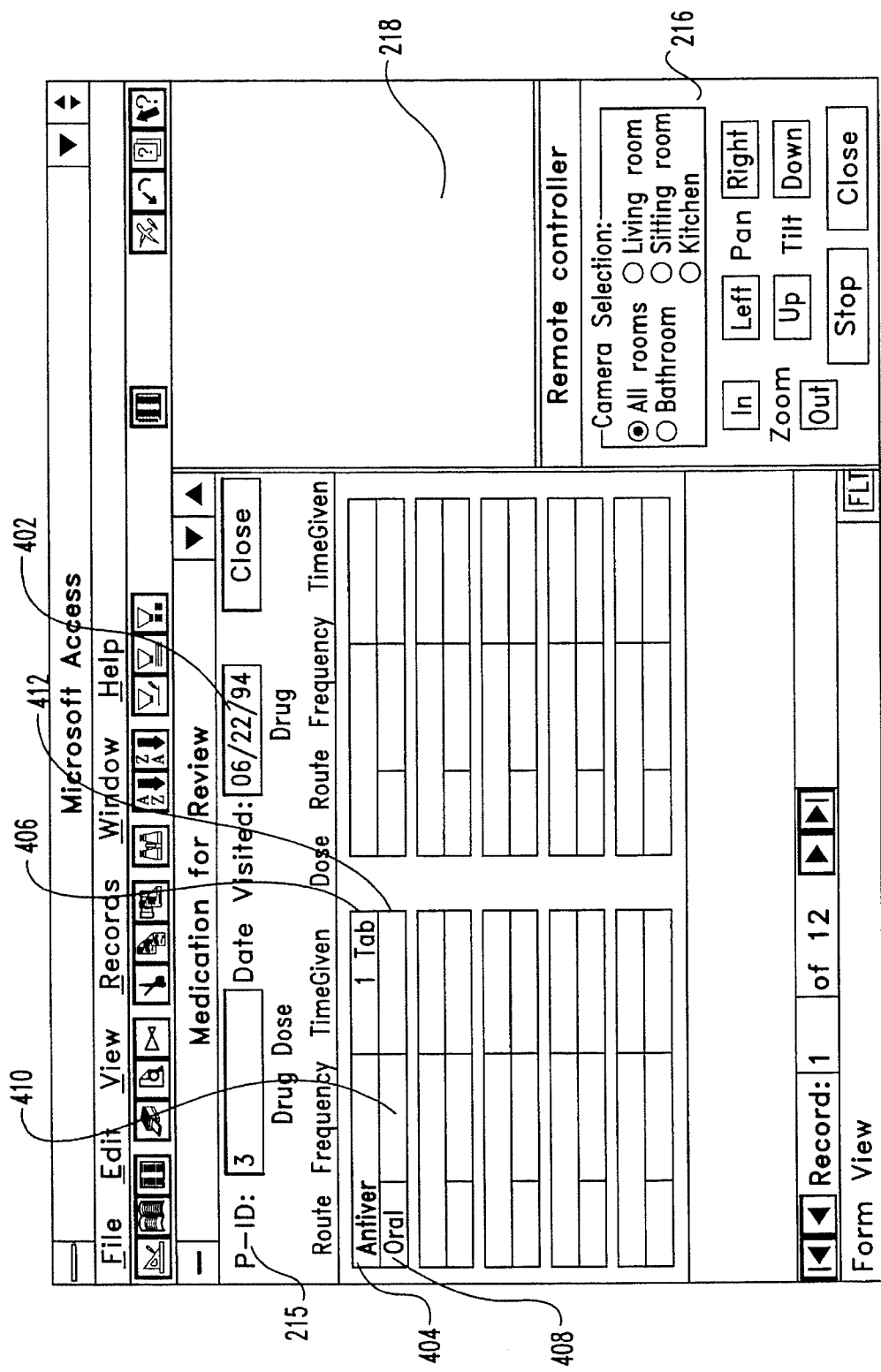
FIG. 15 is a graphical representation of a Medication Review option within the user interface program.

Referring again to FIG. 9, another option within an "in-home" visit is a "Med-" option 230 which provides a "Medication for Review" screen 400 as shown in FIG. 15. As with the previous screens, the right portions 216 and 218 are identical to screen 270 of FIG. 11 and will therefore not be discussed further. The medication screen 400 includes certain identifying information such as, for example patient identification number 215 and date visited 402. Screen 400 further includes a log of drug information for each drug prescribed to the patient 215. For example, the medication screen 400 includes drug name 404, dosage 406, route administered (oral, topical, etc.) 408, prescribed frequency 410 and time administered 412.

Referring again to FIG. 9, another option within an "in-home" visit is a "Newmd" option 232 which provides a new, or blank, "Medication for Review" screen (not shown) identical to screen 400 for new patients and/or new conditions arising with existing patients.

Figure 16:
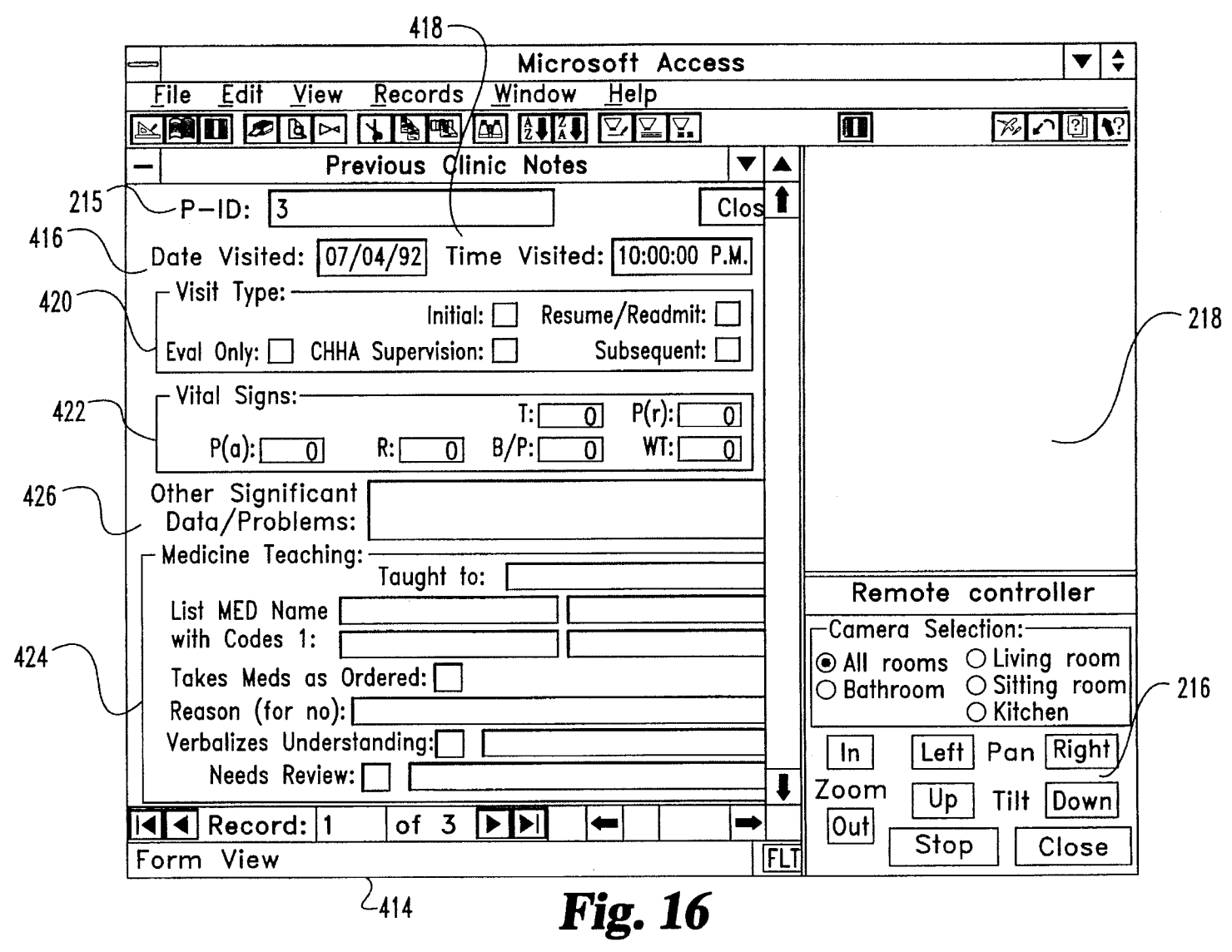

Referring again to FIG. 9, another option within an "in-home" visit is a "PreC" option 234 which provides a "Previous Clinic Notes" screen 414 as shown in FIG. 16. As with the previous screens, the right portions 216 and 218 are identical to screen 270 of FIG. 11 and will therefore not be discussed further. The previous clinic notes 414 includes certain identifying information such as, for example patient identification number 215, date visited 416 and time visited 418. Screen 414 further includes visitation and supervisory information as most clearly shown in its expanded form in FIG. 17. For example, screen 414 includes an indication of the visit type 420; ie. whether it was an initial visit, an evaluational visit, or an actual "in-home" visit by a health care professional, for example, vital patient signs 422 including, for example temperature, blood pressure, weight, etc., medical teaching information 424, Certified Home Health Care supervision information 428, patient evaluation and plans for next visit 430 and a pair of goals sections 432 and 434.

Referring again to FIG. 9, another option within an "in-home" visit is a "NewCli" option 236 which provides a new, or blank, "Clinical Notes" screen (not shown) identical to screen 414 for new patients and/or new conditions arising with existing patients.

Figure 18:
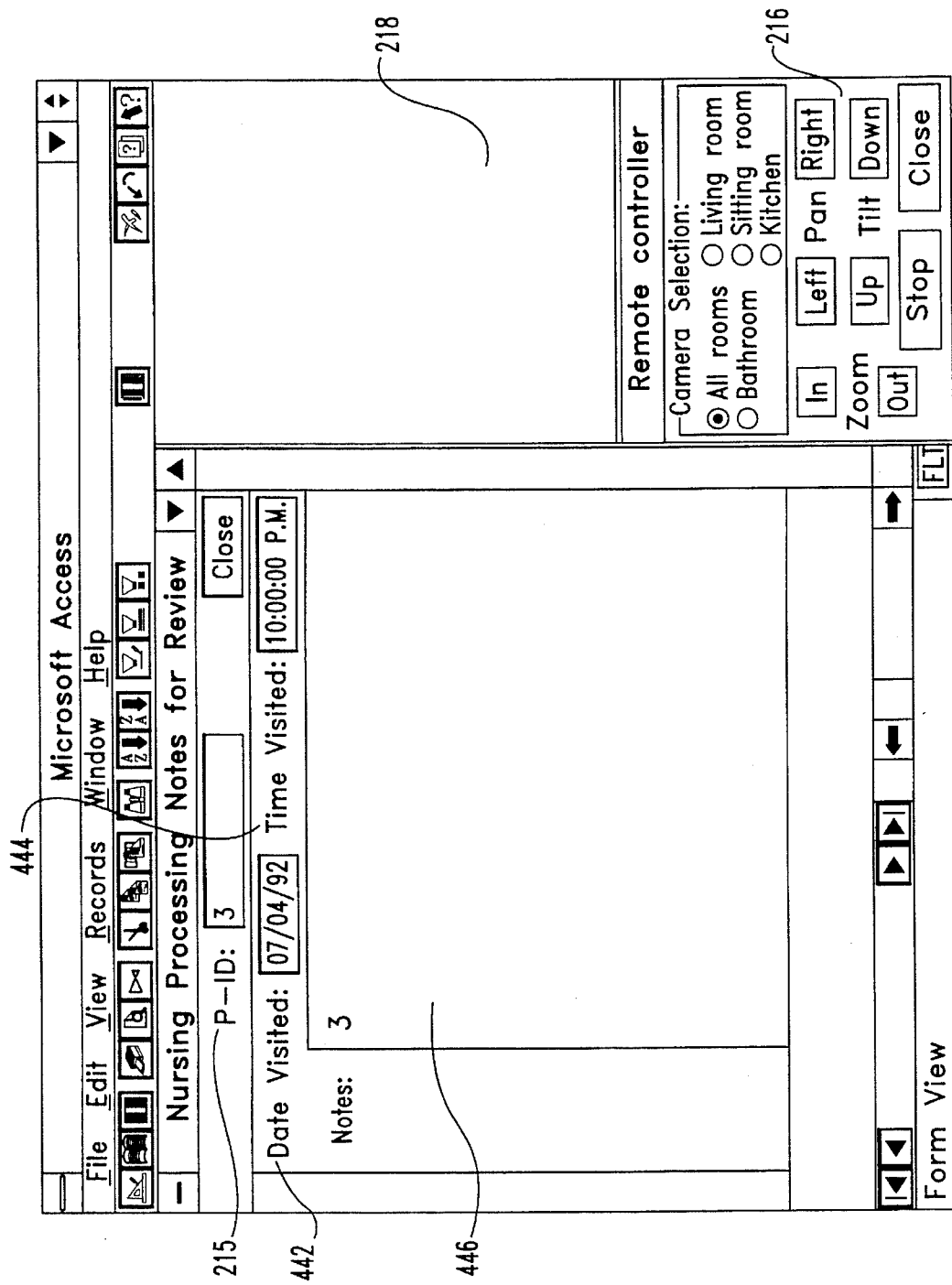
FIG. 18 is a graphical representation of a Notes for Review option within the user interface program.

Referring again to FIG. 9, another option within an "in-home" visit is a "Form" option 238 which provides one of a number of preexisting forms 242-256 for use by the home health care professional. The first form option is "NtP" 242 which produces a "Notes for Review" screen 440 as shown in FIG. 18. As with the previous screens, the right portions 216 and 218 are identical to screen 270 of FIG. 11 and will therefore not be discussed further. The Notes for review screen 440 includes certain identifying information such as, for example, patient identification number 215, date visited 442 and time visited 444. Screen 440 further includes a section 446 for permitting the health care professional to keep a log, or diary, of information regarding the particular patient. The "NtN" option 244 of FIG. 9 (not shown) is a new or blank form version of screen 440 and will not be further discussed.

Figure 19:
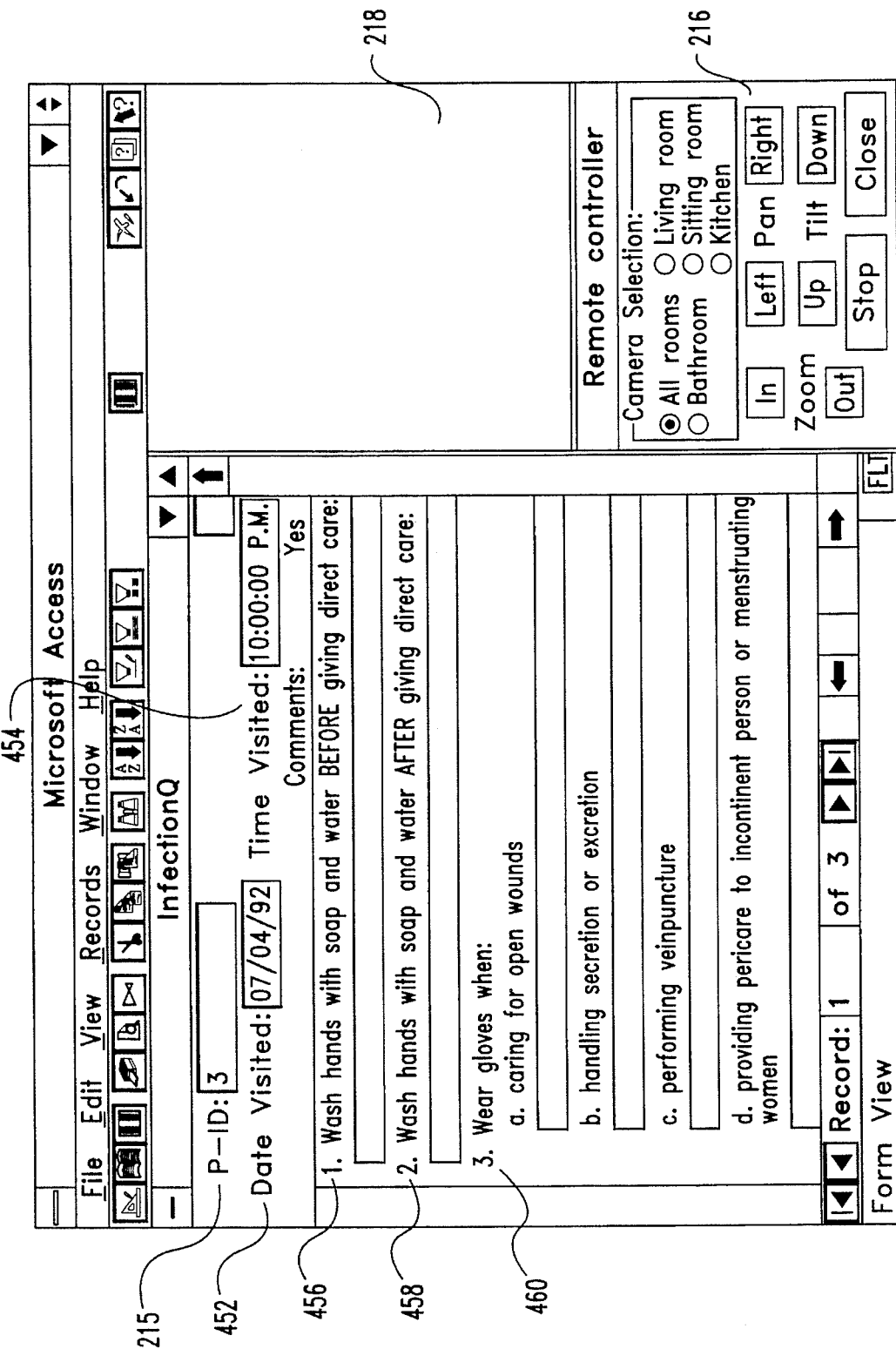
FIG. 19 is a graphical representation of an instructional care form option within the user interface program for providing infection care instructions.
Figure 20:
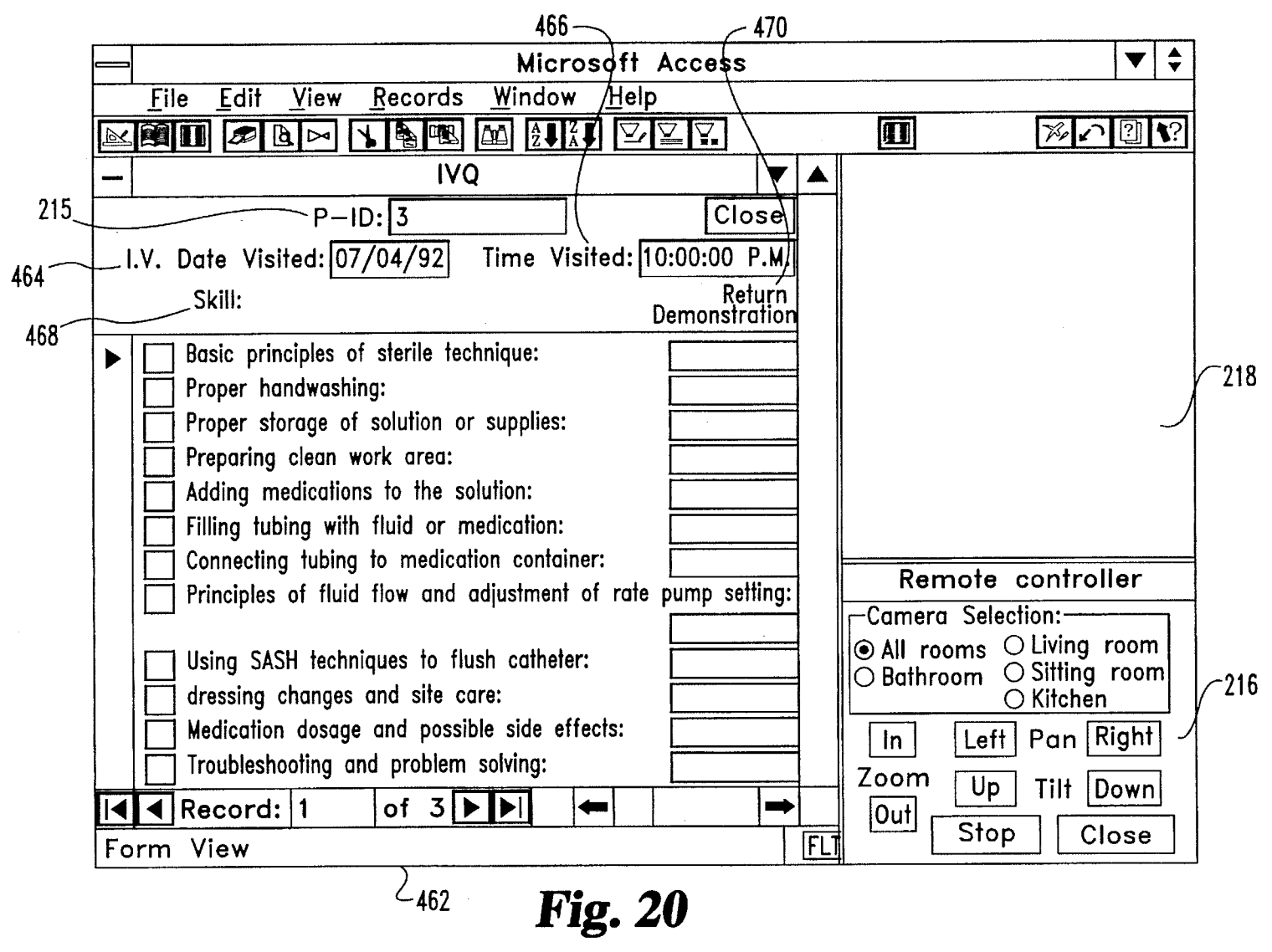

Referring again to FIG. 9, another option within the "Form" options is "IfP" 246 which produces an "InfectionQ" screen 450 as shown in FIG. 19. As with the previous screens, the right portions 216 and 218 are identical to screen 270 of FIG. 11 and will therefore not be discussed further. The InfectionQ screen 450 includes certain identifying information such as, for example, patient identification number 215, date visited 452 and time visited 454. Screen 450 further includes instructions 456, 458 and 460 for the home health care professional to follow, and/or to pass along to the patient, when treating an infection. The present invention contemplates the incorporation of several of such training forms into the user interface to assist the health care professional in either performing, or teaching, a particular procedure. Another such training form, the "IVP" form 250, is selectable from screen 208 of FIG. 9 and produces the IVQ screen 462 as shown in FIG. 20. The IVQ, screen 462 includes certain identifying information such as, for example, patient identification number 215, date visited 464 and time visited 466. As shown in greater detail in FIG. 21, screen 462 further includes guidelines for performing and/or instructing skills 468 associated with intravenous techniques. Screen 462 further provides a Return Demonstration portion 470 and comments portion 472 to indicate further training. The "IfN" option 248 and "IVN" option 252 of FIG. 9 (not shown) are a new or blank forms corresponding to screens 450 and 462 respectively, and will not be further discussed.

Figure 22:
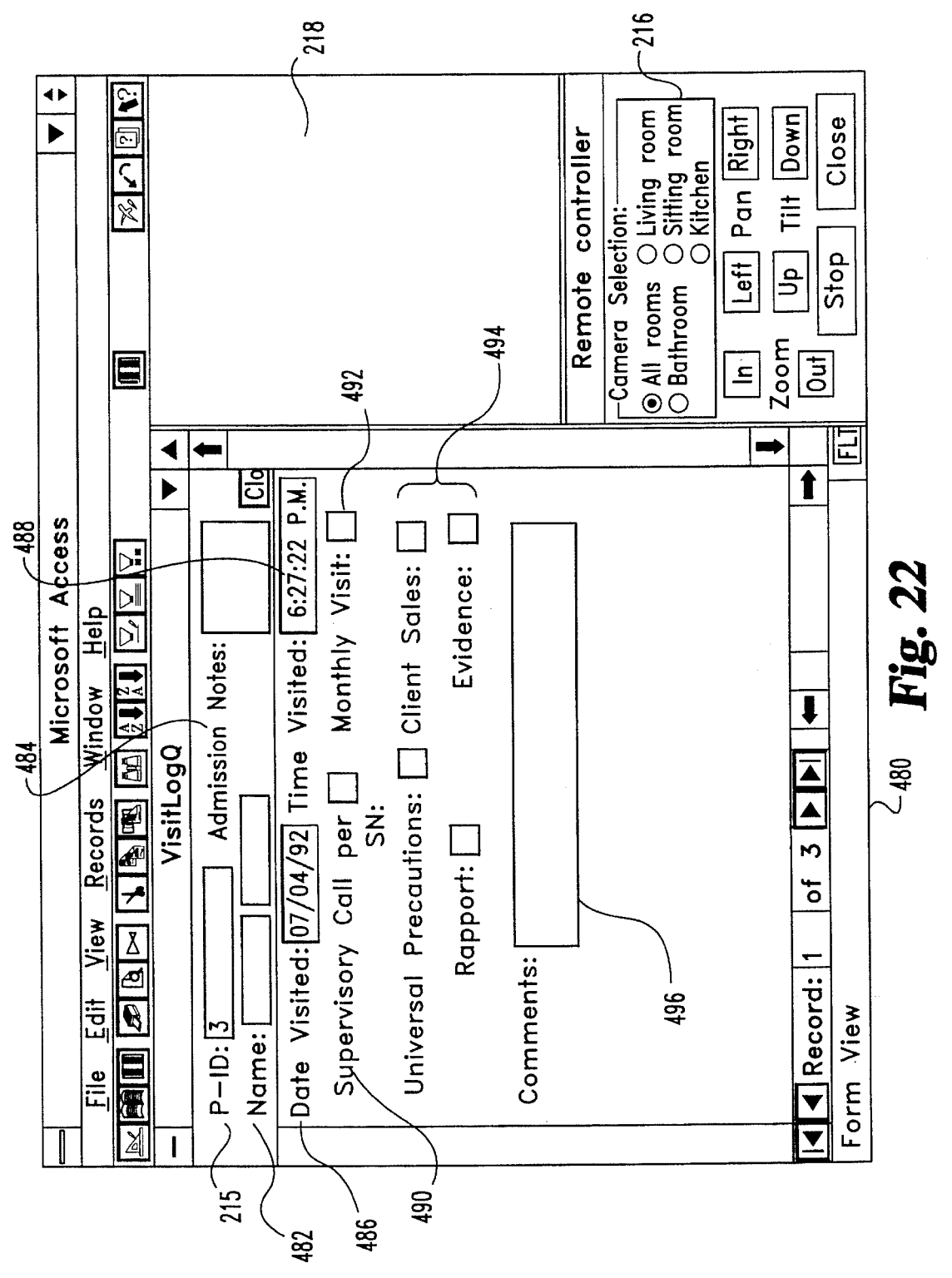

Referring once more to FIG. 9, a final set of options within the "Form" option is "VLP" 254 and "VLN" 256 which produce a "Visit Log" screen 480 as shown in FIG. 22. As with the previous forms, the suffix "P" indicates an existing form and the suffix "N" indicates a new or blank form. As with the previous screens, the right portions 216 and 218 of screen 480 are identical to screen 270 of FIG. 11 and will therefore not be discussed further. The Visit Log screen 480 includes certain identifying information such as, for example, patient identification number 215, patient name 482, patient admission notes 484, date visited 486 and time visited 488. Screen 480 further includes information with regard to the status of the visit including whether the visit was a supervisory call 490 or a monthly visit 492, for example. The screen 480 further includes key health care staff identifying information 494 for use when monitoring care provided to clients. Finally, screen 480 has a section 496 for storing visitation notes prior to terminating the visit. The user interface may be exited by selecting the "quit" option 240 in screen 208 of FIG. 11.

It can be appreciated that with real-time video, real time audio and a variety of textual information relating to a patient, a vast amount of multimedia patient information may be generated to further form a "multimedia medical chart" to replace present-day manually recorded and maintained paper medical charts. With the present system, paper medical charts are replaced with a multimedia medical chart which may be automatically generated in a variety of formats and easily stored on, for example, a write once read many (WORM) storage system such as a CD ROM-based storage system. A multimedia medical chart provides significant advantages over paper medical charts by providing a health care professional with both video and audio records of patient conduct, progress, lack of progress, demeanor, etc. as well as concise textual information that can be rapidly searched via computer 60 for desired information. Moreover, the vast amount of multimedia data relating to the patient and maintained within the patient database may be provided, or formatted, according to any of a number of criteria to suit a particular health care professionals needs.

It is to be understood that the terms "selecting" and "choosing" used in the foregoing user interface description may include a variety of known methods for activating a desired function. Preferably, the user interface includes a plurality of on-screen switches, as is commonly known in windows applications, which may be activated by "clicking" on the switches with a control "mouse", or otherwise selecting and activating the switches with some type of operator input device. It is to be further understood that each of the foregoing screen displays has associated therewith the ability to edit, print, close the present window, quit the application, save data, and other functions commonly associated with windows applications, which can be activated in the manner just described.

Finally, the present invention contemplates that further control signals may be sent to the various SMS computers 60 via corresponding operator commands provided by the health care professional at an MMS computer 40 to perform additional functions within the patient's home. As one example, the present invention contemplates that a plurality of robots may be placed in a patient's home for carrying out tasks, directed in real-time, by the health care professional in a manner previously discussed. Robots may thus be used to administer medication, perform cleaning functions, prepare meals, and perform various other tasks under the direction of the health care professional via the MMS computer 40.

As a second example, the present invention contemplates that a plurality of sensors may be placed in a patient's home to detect various patient data under the direction of the health care professional via the MMS computer 40. The sensors may require patient interaction to provide the data, or may be connected beforehand, for example, to a bedridden patient so that data may be obtained by the health care professional without patient interaction. In either case, the sensors will provide real-time data with respect to, for example, patient weight, blood pressure, body temperature, heartbeat (pulse rate) and blood sugar.

As a further example, the present invention contemplates that a plurality of sensors and actuators may be placed within the patient's home for controlling the operating condition of various home features in real time under the direction of the health care professional via the MMS computer 40. Such sensors and actuators may be used to control, for example, a cooking stove, microwave oven, television, radio, home lighting system, home heating/air conditioning system, door locks and any other household appliance or function capable of real time remote control.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, it is to be understood that the invention described herein is not intended to be limited to the health care field. The present invention contemplates a wide variety of applications wherein, for example, a first location may be monitored from a remote location such that video/audio information provided to the remote location may be controlled from the remote location in real time. Other features of the present invention that are described herein are similarly widely applicable.

What is claimed is:

1. A remote monitoring system for permitting a health care professional to provide health care to a patient in the patient's home from a remote location, said system comprising:

a main database system including a first database having patient data stored therein and a second database having health care professional data stored therein;

a supervisory control computer in communication with said main database system, said supervisory control computer having means for assigning at least one patient in said first database to a health care professional in said second database for providing health care thereto;

a master monitoring computer located remote from the patient's home and in communication with said supervisory control computer, said master monitoring computer having a first telephone modem associated therewith for transmitting and receiving data, said master monitoring computer being operable to provide a plurality of operator command signals at said first modem in response to a corresponding plurality of operator commands provided by the health care professional; and a slave monitoring computer located in the patient's home, said slave monitoring computer having a second telephone modem associated therewith for transmitting and receiving data, said slave monitoring system being in communication with said master monitoring computer via a telephone link established between said first and second modems, said slave monitoring computer being responsive to said plurality of operator command signals to transmit real-time multimedia data relating to the patient to said master monitoring computer;

wherein the health care professional may provide real-time health care to the patient in the patient's home from a remote location.

2. The system of claim 1 further including a plurality of slave monitoring computers, each of said plurality of slave monitoring computers being located in a different patient's home;

wherein said supervisory control computer assigns more than one of said plurality of patients from said first database to the health care professional for providing health care thereto.

3. The system of claim 2 further including a plurality of master monitoring computers, each of said master monitoring computers being operable by one of a number of health care professionals;

wherein said supervisory control computer assigns more than one of said plurality of patients to one of said number of health care professionals in said second database for providing health care thereto.

4. The system of claim 3 wherein each of said number of master monitoring computers may communicate with each other via a peer-to-peer network to share said multimedia data corresponding to any of said patients therebetween.

5. The system of claim 1 wherein said supervisory control computer communicates with said main database system via a local area network.

6. The system of claim 5 wherein said supervisory computer communicates with said master monitoring computer via a server/client network scheme.

7. The system of claim 6 wherein each of said patient and health care professional databases are relational databases.

8. The system of claim 1 wherein said master monitoring computer includes a windows-base interface for providing said plurality of operator command signals to said first modem in response to said corresponding plurality of operator commands provided by the health care professional.

9. The system of claim 1 wherein said supervisory control computer further includes means for providing the health care professional with health care information relating to the patient.

10. The system of claim 9 wherein said health care information includes various health maintenance functions to be monitored by the health care professional.

11. The system of claim 1 wherein said master monitoring computer includes means for providing multimedia data relating to the health care professional;

and wherein said slave monitoring computer receives said multimedia data relating to the health care professional in real-time;

whereby the health care professional and patient may communicate with each other in real-time via said system.

12. A remote monitoring system for monitoring a first location from a remote location, said system comprising:

a video camera located in the first location, said video camera providing video signals in accordance with video images captured thereby and being responsive to a plurality of control signals to perform a corresponding plurality video camera functions;

a master monitoring computer located remote from the first location, said master monitoring computer having a first telephone modem associated therewith and a monitor, said master monitoring computer receiving said video signals from said video camera and displaying said corresponding video images on said monitor, and further providing said plurality of control signals to said video camera in response to corresponding operator commands, said master monitoring computer including a windows-based interface for providing said plurality of operator command signals to said video camera in response to said corresponding operator commands; and a slave monitoring computer located in the first location, said slave monitoring computer having a second telephone modem associated therewith and being in communication with said master monitoring computer via a telephone link established between said first and second modems, said slave monitoring computer receiving said video signals from said video camera and providing said video signals to said master monitoring computer via said telephone link, and further receiving said plurality of control signals from said master monitoring computer and providing said control signals to said video camera;

wherein said video camera functions may be controlled in real time from a remote location to thereby view various areas within the first location.

13. The system of claim 12 further including a video camera control unit located within the first location, said control unit receiving said control signals from said slave monitoring computer and providing said control signals to said video camera to thereby cause said video camera to perform said plurality of video camera functions.

14. The system of claim 13 wherein said plurality of video camera functions includes a pan left function;

and further wherein said video camera is responsive to a pan left control signal provided by said control unit in response to a pan left control command to pan said video camera to the left.

15. The system of claim 14 wherein said plurality of video camera functions includes a pan right function;

and further wherein said video camera is responsive to a pan right control signal provided by said control unit in response to a pan right control command to pan said video camera to the right.

16. The system of claim 13 wherein said plurality of video camera functions includes a tilt up function;

and further wherein said video camera is responsive to a tilt up control signal provided by said control unit in response to a tilt up control command to tilt said video camera upwardly.

17. The system of claim 16 wherein said plurality of video camera functions includes a tilt down function;

and further wherein said video camera is responsive to a tilt down control signal provided by said control unit in response to a tilt down control command to tilt said video camera downwardly.

18. The system of claim 13 wherein said plurality of video camera functions includes a zoom in function;

and further wherein said video camera is responsive to a zoom in control signal provided by said control unit in response to a zoom in control command to increase the magnification of said video camera.

19. The system of claim 18 wherein said plurality of video camera functions includes a zoom out function;

and further wherein said video camera is responsive to a zoom out control signal provided by said control unit in response to a zoom out control command to decrease the magnification of said video camera.

20. The system of claim 12 wherein the first location includes a plurality of rooms and wherein the system further includes at least one of said video cameras located in at least one of said plurality of rooms within the first location, each of said video cameras being controllable by said master monitoring computer in response to operator command signals.

21. The system of claim 20 further including a video camera switching unit located within the first location, said switching unit receiving said video signals from said plurality of video cameras and being responsive to a camera selection control signal, provided by said master monitoring computer in response to a corresponding video camera selection operator command, to provide said video signals from a selected one of said video cameras to said master monitoring computer.

22. The system of claim 12 wherein said operator commands are provided by activating on-screen switches within said windows-based interface.

23. The system of claim 12 further including a microphone located within the first location, said microphone providing audio signals corresponding to audible sounds created within the first location, said slave monitoring computer receiving said audio signals from said microphone and providing said audio signals to said master monitoring computer via said telephone link, said master monitoring computer including means for replicating said audio signals at an audible level;

wherein said audio signals may be received in real time.

24. The system of claim 23 wherein the first location includes a plurality of rooms and wherein the system further includes at least one of said microphones located in at least one of said plurality of rooms within the first location, each of said microphones being controllable by said master monitoring computer in response to operator command signals.

25. The system of claim 23 wherein said master monitoring computer includes means for recording at least one of said video images displayed on said monitor and said audio signal.

26. The system of claim 23 wherein said master monitoring computer further includes a video camera and a microphone for transmitting multimedia data relating to a master monitoring computer operator to said slave monitoring computer;

and wherein said slave computer may receive real-time multimedia data relating to said operator.

27. The system of claim 23 wherein said master monitoring computer further includes a video camera and a microphone for transmitting multimedia data provided by a master monitoring computer operator to said slave monitoring computer;

and wherein said slave computer may receive real-time multimedia data provided by said operator.

28. The system of claim 12 wherein the first location is a patient's home and the master monitoring computer receives said operator commands from a health care professional.

29. A remote monitoring system for permitting a health care professional to provide health care to a patient in the patient's home from a remote location, said system comprising:

means located within the patient's home for generating real-time multimedia data relating to the patient, said multimedia data including video data;

a slave monitoring computer located in the patient's home, said slave monitoring computer having a first telephone modem associated therewith for transmitting and receiving data, said slave monitoring computer receiving said multimedia data and transmitting said multimedia data at said first modem;

a first database having multimedia patient data stored therein; and a master monitoring computer located remote from the patient's home, said master monitoring computer having a monitor and a second telephone modem associated therewith for transmitting and receiving data, said master monitoring computer being in communication with said slave monitoring computer via a telephone link established between said first and second modems, said master monitoring computer receiving said multimedia data at said second modem and displaying said multimedia data on said monitor, said master monitoring computer further being responsive to an operator command signal corresponding to an operator command provided by the health care professional to automatically store said multimedia data within said first database to thereby maintain a multimedia medical log of the patient's medical treatment, said master monitoring computer including means for generating multimedia data, including video data, relating to the health care professional, said master monitoring computer transmitting said multimedia data relating to the health care professional to said slave monitoring computer such that the patient may observe said multimedia data relating to the health care professional in real-time;

wherein multimedia medical data relating to the patient and generated within the patient's home may be received and maintained by a health care professional from a remote location.

30. The system of claim 29 wherein said means for generating multimedia data includes a video camera, and said multimedia data includes real-time video transmission of the patient's activities.

31. The system of claim 30 wherein said means for generating multimedia data includes a microphone, and said multimedia data includes real-time audio transmission of audible sounds created within the patient's home.

32. The system of claim 31 wherein said master monitoring computer includes means for receiving operator-generated text;

and wherein said multimedia medical log may include said operator-generated text.

33. The system of claim 29 further including means for monitoring said multimedia data transmission and alerting one of the patient and the health care professional in response to a predetermined condition detected within said multimedia data.

34. The system of claim 33 wherein said predetermined condition includes a failure of the patient comply with prescribed medical treatment.

35. The system of claim 33 wherein said predetermined condition includes a lack of patient activity within a predetermined time period.

36. The system of claim 33 wherein said predetermined condition includes a distress signal generated by the patient.

37. The system of claim 29 wherein said means associated with said master monitoring computer for generating multimedia data relating to the health care professional includes at least one of a video camera and a microphone.

38. The system of claim 29 further including means associated with said master monitoring computer for generating multimedia data provided by the health care professional;

wherein said master monitoring computer transmits said multimedia data provided by the health care professional to said slave monitoring computer such that the patient may observe said multimedia data provided by the health care professional in real-time.

39. The system of claim 38 wherein said means associated with said master monitoring computer for generating multimedia data provided by the health care professional includes a video cassette recorder.

40. A method of providing health care to a patient in the patient's home from a remote location, said method comprising the steps of:

(1) providing a first computer at the remote location;

(2) providing a second computer in the patient's home;

(3) linking said first and second computers to each other for communication therebetween;

(4) providing means for generating real-time multimedia data relating to the patient within the patient's home, said multimedia data including video data;

(5) transmitting said real-time multimedia data relating to the patient to said first computer;

(6) providing means associated with said first computer for generating real-time multimedia data, including video data, relating to the health care professional;

(7) transmitting said real-time multimedia data relating to the health care professional to the patient's home;

(8) observing the patient in real-time from said remote location via said multimedia data relating to the patient and observing the health care professional in real-time from the patient's home via said multimedia data relating to the health care professional; and (9) communicating with the patient in real-time via said communications link to thereby provide the patient with health care from said remote location.

41. The method of claim 40 wherein said means for generating said multimedia data relating to the patient includes a video camera;

and wherein said real-time multimedia data relating to the patient includes video images of the patient.

42. The method of claim 41 wherein said means for generating said multimedia data relating to the patient includes a microphone;

and wherein said real-time multimedia data relating to the patient includes audio reproduction of audible sounds created within the patient's home.

43. The method of claim 41 wherein said video camera further includes means for performing a plurality of video camera functions;

and wherein said video camera is responsive to operator control signals generated by a health care professional at said first computer to actuate said plurality of video functions;

and further wherein step (5) includes generating said operator control signals at said first computer to actuate said plurality of video camera functions to thereby facilitate the transmission and reception of said video signals.

44. The method of claim 43 wherein said plurality of video camera functions include at least one of pan left, pan right, tilt up, tilt down, zoom in and zoom out.

45. The method of claim 40 wherein said means for generating said multimedia data relating to the health care professional includes at least one of a video camera and a microphone;

and wherein said real-time multimedia data relating to the health care professional includes at least one of video images of the health care professional and audio reproduction of audible sounds provided by the health care professional.

46. A remote monitoring system for permitting a health care professional to provide health care to a patient in the patient's home from a remote location, said system comprising:

a robot located in the patient's home, said robot being responsive to a control signal to perform a health care related function;

a master monitoring computer located remote from the patient's home, said master monitoring computer having a first telephone modem associated therewith for providing said control signal to said robot in response to a corresponding operator command provided by the health care professional; and a slave monitoring computer located in the patient's home, said slave monitoring computer having a second telephone modem associated therewith and being in communication with said master monitoring computer via a telephone link established between said first and second modems, said slave monitoring computer receiving said control signal from said master monitoring computer and providing said control signal to said robot;

wherein the health care professional may control said robot functions in real time from a remote location to thereby provide an aspect of home health care by performing said health care related function via said robot.

47. The system of claim 46 wherein said health care related function includes administering medication to the patient.

48. A remote monitoring system for permitting a health care professional to provide health care to a patient in the patient's home from a remote location, said system comprising:

a sensor located in the patient's home, said sensor being responsive to a control signal to sense a bodily condition of the patient, said sensor providing a sensor signal corresponding to said sensed condition;

a master monitoring computer located remote from the patient's home, said master monitoring computer having a first telephone modem associated therewith for providing said control signal to said sensor in response to a corresponding operator command provided by the health care professional, said master monitoring computer receiving said sensor signal via said first modem and having means associated therewith for determining said bodily condition from said sensor signal; and a slave monitoring computer located in the patient's home, said slave monitoring computer having a second telephone modem associated therewith and being in communication with said master monitoring computer via a telephone link established between said first and second modems, said slave monitoring computer receiving said control signal from said master monitoring computer and providing said control signal to said sensor;

wherein the health care professional may control said sensor in real time from a remote location to thereby provide an aspect of home health care by determining said bodily condition.

49. The system of claim 48 wherein said bodily condition includes at least one of the patient's weight, blood pressure, body temperature, heart rate and blood sugar.

50. A remote monitoring system for permitting a health care professional to provide health care to a patient in the patient's home from a remote location, said system comprising:

an actuator located in the patient's home, said actuator being responsive to a control signal to actuate and deactuate a home feature;

a sensor associated with said actuator, said sensor sensing the operating status of said home feature and providing a sensor signal corresponding thereto;

a master monitoring computer located remote from the patient's home, said master monitoring computer having a first telephone modem associated therewith for providing said control signal to said actuator in response to a corresponding operator command provided by the health care professional, said master monitoring computer receiving said sensor signal via said first modem and having means associated therewith for determining the operating status of said home feature from said sensor signal; and a slave monitoring computer located in the patient's home, said slave monitoring computer having a second telephone modem associated therewith and being in communication with said master monitoring computer via a telephone link established between said first and second modems, said slave monitoring computer receiving said control signal from said master monitoring computer and providing said control signal to said actuator;

wherein the health care professional may control said home feature in real time from a remote location to thereby provide an aspect of home health care.

51. The system of claim 50 wherein said home feature includes at least one of a cooking stove, microwave oven, television, radio, home lighting system, home heating/air conditioning system and door locks.

* * * * *